United States Patent [19]

Toriuchi et al.

[11] Patent Number: 4,939,066

[45] Date of Patent: * Jul. 3, 1990

[54] COLOR DIFFUSION TRANSFER PHOTOGRAPHIC ELEMENT

[75] Inventors: Masaharu Toriuchi; Keizo Koya, both of Kanagawa, Japan

[73] Assignee: Fuji Photo Film Co., Ltd., Kanagawa, Japan

[*] Notice: The portion of the term of this patent subsequent to Nov. 8, 2005 has been disclaimed.

[21] Appl. No.: 115,070

[22] Filed: Oct. 30, 1987

[30] Foreign Application Priority Data

Oct. 30, 1986 [JP] Japan .................................. 61-259326

[51] Int. Cl.$^5$ .............................................. G03C 5/54
[52] U.S. Cl. ..................................... 430/219; 430/957; 430/223
[58] Field of Search ................ 430/219, 223, 957, 559

[56] References Cited

U.S. PATENT DOCUMENTS

| | | | |
|---|---|---|---|
| 4,139,379 | 2/1979 | Chasman et al. | 430/223 |
| 4,450,223 | 5/1984 | Van Poucke et al. | 430/219 |
| 4,499,181 | 2/1985 | Watanabe et al. | 430/223 |

Primary Examiner—Richard L. Schilling
Attorney, Agent, or Firm—Sughrue, Mion, Zinn, Macpeak & Seas

[57] ABSTRACT

A color diffusion transfer photographic material comprises a base having thereon at least one silver halide emulsion layer and a dye image-receiving layer, at least one layer thereof containing a dye-releasing redox compound and at least one layer thereof containing a development inhibitor-releasing compound represented by the following general formula (I):

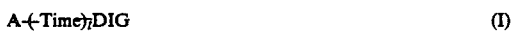

(I)

wherein A represents

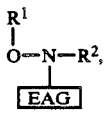

linked to $-(Time)_t$-DIG through at least one of $R^1$, $R^2$ and EAG; $R^1$ and $R^2$, which may be the same or different, each represents a single bond or a substituent other than a hydrogen atom, provided that $R^1$ and $R^2$ may be linked to form a ring; EAG represents an electron-accepting group; Time represents a group capable of releasing DIG after EAG accepts an electron; DIG represents a development inhibitor precursor; and t is an integer of 0 or 1.

15 Claims, No Drawings

COLOR DIFFUSION TRANSFER PHOTOGRAPHIC ELEMENT

FIELD OF THE INVENTION

The invention relates to a color diffusion transfer photographic element and, particularly, to a color diffusion transfer photographic element containing a novel development inhibitor-releasing compound.

BACKGROUND OF THE INVENTION

It is known to use various fogging preventive techniques to obtain an image having reduced fogging (hereinafter referred to as "Dmin", Dmin being the lowest image density region of a final image) and a clean white background in the image, and it is typical to use a development inhibitor or a precursor thereof.

Examples of development inhibitors (including development inhibitor precursors) are described, for example, in Japanese Patent Application (OPI) Nos. 89034/75, 155837/79, 95539/85 and 144737/85 (the term "OPI" as used herein refers to a "published unexamined Japanese patent application").

If sufficient fog inhibition is attained using the above development inhibitors or their precursors, the required development is also disadvantageously inhibited That is, if a strong development inhibitor is used or a large amount of a development inhibitor is used, generally the amount of developed silver is substantially reduced or the development rate is substantially lowered. In a color diffusion transfer process that uses dye-releasing redox compounds that can release dyes by silver development and a direct reversal emulsion, the maximum density (Dmax) is lowered and the development rate required to complete the image is lowered. The delay to complete an image is a serious disadvantage in the case of instant photography, wherein the ability to produce a picture quickly is very important.

The development of an effective development inhibitor free from such disadvantages has long been desired.

SUMMARY OF THE INVENTION

A first object of the invention is a novel development inhibitor that can lower the Dmin without delay to complete an image.

A second object of the invention is to provide a photographic element for the color diffusion transfer process that contains a development inhibitor capable of lowering the Dmin.

After studying keenly, the present inventors now have found that these and other objects of the present invention can be attained by a color diffusion transfer photographic material comprising a base having thereon at least one silver halide emulsion layer and a dye image-receiving layer, at least one layer thereof containing a dye-releasing redox compound and at least one layer thereof containing a development inhibitor-releasing compound represented by the following general formula (I):

$$A-(Time)_t DIG \quad (I)$$

wherein A represents

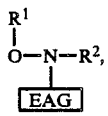

linked to $-(Time)_t DIG$ through at least one of $R^1$, $R^2$ and EAG; $R^1$ and $R^2$, which may be the same or different, each represents a single bond or a substituent other than a hydrogen atom, provided that $R^1$ and $R^2$ may be linked to form a ring; EAG represents an electron-accepting group; Time represents a group capable of releasing DIG after EAG accepts an electron; DIG represents a development inhibitor precursor; and t is an integer of 0 or 1.

DETAILED DESCRIPTION OF THE INVENTION

The compounds represented by general formula (I) are development inhibitor-releasing compounds, and to enhance the characteristics and to increase the degree of freedom of their synthesis, the compounds represented by general formula (I) are preferably compounds represented by the following general formula (II):

$$A'-(Time)_t DIG \quad (II)$$

wherein A' represents

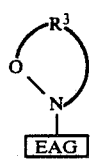

linked to $-(Time)_t DIG$ through at least one of $R^3$ and EAG; $R^3$ represents an atomic group required to form a 3- to 8-membered single or condensed heterocyclic ring together with the nitrogen atom and the oxygen atom; and EAG, Time, t and DIG each has the same meaning as in general formula (I).

The present development inhibitor-releasing (hereinafter "DIR") compound is reduced with a reducing agent present during processing, so that the nitrogen-oxygen bond is cleaved and through a subsequent electron transfer a development inhibitor is released. In an image area where silver development takes place to a greater extent, the amount of the reducing material present is correspondingly reduced, so that the DIR compound would not be reduced to release a development inhibitor to the same extent.

The DIR compounds according to the invention are now described in greater detail.

Development inhibitor precursors represented by DIG may be prepared by a well known process and can include any of known development inhibitors.

Examples of the development inhibitors are compounds having a mercapto group attached to a heterocyclic ring such as substituted or unsubstituted mercaptotriazoles (e.g., 1-phenyl-5-mercaptotetrazole, 1-(4-carboxyphenyl)-5-mercaptotetrazole, 1-(3-hydroxyphenyl)-5-mercaptotetrazole, 1-(4-sulfophenyl)-5-mercaptotetrazole, 1-(3-sulfophenyl)-5-mercaptotetrazole, 1-(4-sulfamoylphenyl)-5-mercaptotetrazole, 1-(3-hexanoylaminophenyl)-5-mercaptotetrazole, 1-ethyl-5-mercaptotetrazole, 1-(2-carboxyethyl)-5-mercaptotetrazole, 2-methylthio-5-mercapto-1,3,4-thiadiazole, 2-(2-carboxyethylthio)-5-mercapto-1,3,4-thiadiazole, 3-methyl-4-phenyl-5-mercapto-1,2,4-thiadiazole, 2-(2-dimethylaminoethylthio)-5-mercapto-1,3,4-thiadiazole, 1-(4-n-hexylcarbamoylphenyl)-2-mercaptoimidazole, 3-acetylamino-4-methyl-5-mercapto-1,2,4-thiadiazole, 2-mercaptobenzoxazole, 2-mercaptobenzimidazole, 2-mercaptobenzothiazole, 2-mercapto-6-nitro-1,3-benzoxazole, 1-(1-naphthyl)-5-mercaptotetrazole, 2-phenyl-5-mercapto-1,3,4-oxadiazole, 1-[3-(3-methylureido)-phenyl]-5-mercaptotetrazole, 1-(4-nitrophenyl)-5-mercaptotetrazole and 5-(2-ethylhexanoylamino)-2-mercaptobenzimidazole), substituted or unsubstituted mercaptoazaindenes (e.g., 6-methyl-4-mercapto-1,3,3a,7-tetraazaindene, 6-methyl-2-benzyl-4-mercapto-1,3,3a,7-tetraazaindene, 6-phenyl-4-mercaptotetraazaindene and 4,6-dimethyl-2-mercapto-1,3,3a,7-tetraazaindene) and substituted or unsubstituted mercaptopyrimidines (e.g., 2-mercaptopyrimidine, 2-mercapto-4-methyl-6-hydropyrimidine and 2-mercapto-4-propylpyrimidine). Further examples are heterocyclic compounds capable of forming silver imino compounds such as substituted or unsubstituted benzotriazoles (e g., benzotriazole, 5-nitrobenzotriazole, 5-methylbenzotriazole, 5,6-dichlorobenzotriazole, 5-bromobenzotriazole, 5-methoxybenzotriazole, 5-acetylaminobenzotriazole, 5-n-butylbenzotriazole, 5-nitro-6-chlorobenzotriazole, 5,6-dimethylbenzotriazole and 4,5,6,7-tetrachlorobenzotriazole), substituted or unsubstituted indazoles (e.g., indazole, 5-nitroindazole, 3-nitroindazole, 3-chloro-5-nitroindazole, 3-cyanoindazole, 3-n-butylcarbamoylindazole and 5-nitro-3-methanesulfonylindazole) and substituted or unsubstituted benzimidazoles e.g., 5-nitrobenzimidazole, 4-nitrobenzimidazole, 5,6-dichlorobenzimidazole, 5-cyano-6-chlorobenzimidazole and 5-trifluoromethyl-6-chlorobenzimidazole). Those development inhibitors can also be used that will undergo a reaction subsequent to an oxidation reduction reaction in a development processing step to release from the oxidation reduction mother nucleus of general formula (I) a compound having a development inhibiting property, which compound in turn will subsequently further react to form a compound having substantially no development inhibiting property or having a remarkably reduced development inhibiting property. Such a two-step development generally utilizes a hydrolysis of esters Specific examples of such development inhibitors are 1-(3-phenoxycarbonylphenyl)-5-mercaptotetrazole, 1-(4-phenoxycarbonylphenyl)-5-mercaptotetrazole, 1-(3-maleinimidophenyl)-5-mercaptotetrazole, 5-(phenoxycarbonyl)benzotriazole, 5-(p-cyanophenoxycarbonyl)benzotriazole, 2-phenoxycarbonylmethylthio-5-mercapto-1,3,4-thiadiazole, 5-nitro-3-phenoxycarbonylindazole, 5-phenoxycarbonyl-2-mercaptobenzimidazole, 5-(2,3-dichloropropyloxycarbonyl)benzotriazole, 5-benzyloxycarbonylbenzotriazole, 5-(butylcarbamoylmethoxycarbonyl)benzotriazole, 5-(butoxycarbonylmethoxycarbonyl)benzotriazole, 1-(4-benzoyloxyphenyl)-5-mercaptotetrazole, 5-(2-methanesulfonylethoxycarbonyl)-2-mercaptobenzothiazole, 1-[4-(2-chloroethoxycarbonyl)phenyl]-2-mercaptoimidazole, 2-[3-(thiophen-2-ylcarbonyl)propyl]-thio-5-mercapto-1,3,4-thiadiazole, 5-cinnamoylaminobenzotriazole, 1-(3-vinylcarbonylphenyl)-5-mercaptotetrazole, 5-succinimidomethylbenzotriazole, 2-(4-succinimidophenyl)-5-mercapto-1,3,4-oxadiazole, 3-[4-(benzo-1,2-isothiazole-3-oxo-1,1-dioxy-2-yl)phenyl]-5-mercapto-4-methyl-1,2,4-triazole and 6-phenoxycarbonyl-2-mercaptobenzoxazole.

Furthermore, DIG may be replaced by DYE, which is dye part, to form a dye-releasing redox compound.

In general formula (I), EAG represents a group capable of accepting an electron from a reducing material, and linked to the nitrogen atom. Preferably, EAG is a group represented by the following general formulae (A) or (B):

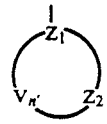
(A)

(B)

In general formula (A), $Z_1$ represents

or

$V_{n'}$ represents atomic group(s) necessary for forming a 3- to 8-membered ring together with $Z_1$ and $Z_2$, which may be the same or different, in which n' shows a number of groups V which is an integer of 1 to 6; and $Z_2$ and group of $V_{n'}$ each represents

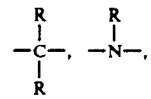

—O—, —S— or —SO$_2$—; and R represents a bond (a π-bond), a hydrogen atom or one of substituents given below, provided that plural R groups may be the same or different, and substituents represented by R may be linked to form a 3- to 8-membered saturated or unsaturated carbon ring or heterocyclic ring. In general formula (A), the R groups are selected such that the total of the Hammett substituent constants thereof $\sigma_p$ is at least about +0.09, preferably at least about +0.3, and more preferably at least about +0.45. The Hammett substituent constants are referred to *J. Med Chem*, 16, 1207 (1973), Hanoch C., *Structure-Activity Relationship*, Vol. 1 (Cavallico C. F., Ed ), Pergamon Press, New York.

Examples of substituents (wherein preferably the number of carbon atoms is 0 to 40) represented by R include substituted or unsubstituted alkyl groups (e g., a methyl group, an ethyl group, a sec-butyl group, a t-octyl group, a benzyl group, a cyclohexyl group, a chloromethyl group, a dimethylaminomethyl group, an n-hexadecyl group, a trifluoromethyl group, a 3,3,3-trichloropropyl group and a methoxycarbonylmethyl group), substituted or unsubstituted alkenyl groups (e.g., a vinyl group, a 2-chlorovinyl group and a 1-methylvinyl group), substituted or unsubstituted alkynyl groups (e.g., an ethynyl group and a 1-propynyl group), a cyano group, a nitro group, a halogen atom (fluorine, chlorine, bromine and iodine), a substituted or unsubstituted heterocyclic ring residue (e.g., a 2-pyridyl group, a 1-imidazolyl group, a benzothiazol-2-yl group, a morpholino group and a benzoxazol-2-yl group), a sulfo group, a carboxyl group, a substituted or unsubstituted aryloxycarbonyl or alkoxycarbonyl group (e.g., a methoxycarbonyl group, an ethoxycarbonyl group, a tetradecyloxycarbonyl group, a 2-methoxyethylcarbonyl group, a phenoxycarbonyl group, a 4-cyanophenylcarbonyl group and a 2-chlorophenoxycarbonyl group), substituted or unsubstituted carbamoyl groups (e.g., a carbamoyl group, a methylcarbamoyl group, a diethylcarbamoyl group, a methylhexadecylcarbamoyl group, a methyloctadecylcarbamoyl group, a phenylcarbamoyl group, a 2,4,6-trichlorophenylcarbamoyl group, an N-ethyl-N-phenylcarbamoyl group and a 3-hexadecylsulfamoylphenylcarbamoyl group), a hydroxyl group, a substituted or unsubstituted azo group (e.g., a phenylazo group, a p-methoxyphenylazo group and a 2-cyano-4-methanesulfonylphenylazo group), a substituted or unsubstituted aryloxy or alkoxy group (e.g., a methoxy group, an ethoxy group, a dodecyloxy group, a benzyloxy group, a phenoxy group, a 4-methoxyphenoxy group, a 3-acetylaminophenoxy group, a 3-methoxycarbonylpropyloxy group and a 2-trimethylammonioethoxy group), a sulfino group, a sulfeno group, a mercapto group, a substituted or unsubstituted acyl group (e.g., an acetyl group, a trifluoroacetyl group, an n-butyloyl group, a t-butyloyl group, a benzoyl group, a 2-carboxybenzoyl group, a 3-nitrobenzoyl group and a formyl group), a substituted or unsubstituted arylthio or alkylthio group (e.g., a methylthio group, an ethylthio group, a t-octylthio group, a hexadecylthio group, a phenylthio group, a 2,4,5-trichlorothio group, a 2-methoxy-5-t-octylphenylthio group and a 2-acetylaminophenylthio group), a substituted or unsubstituted aryl group (e.g., a phenyl group, a naphthyl group, a 3-sulfophenyl group, a 4-methoxyphenyl group and a 3-lauroylaminophenyl group), a substituted or unsubstituted sulfonyl group (e.g., a methylsulfonyl group, a chloromethylsulfonyl group, an n-octylsulfonyl group, an n-hexadecylsulfonyl group, a sec-octylsulfonyl group, a p-toluenesulfonyl group, a 4-chlorophenylsulfonyl group, a 4-dodecylphenylsulfonyl group, a 4-dodecyloxyphenylsulfonyl group and a 4-nitrophenylsulfonyl group), a substituted or unsubstituted sulfinyl group e.g., a methylsulfinyl group, a dodecylsulfinyl sulfinyl group, a phenylsulfinyl group and a 4-nitrophenyl group), a substituted or unsubstituted amino group (e.g., a methylamino group, a diethylamino group, a methyloctadecylamino group, a phenylamino group, an ethylphenylamino group, a 3-tetradecylsulfamoylphenylamino group, an acetylamino group, a trifluoroacetylamino group, an N-hexadecylacetylamino group, an N-methylbenzoylamino group, a methoxycarbonylamino group, a phenoxycarbonylmethyl group, an N-methoxyacetylamino group, an amidinoamino group, a phenylaminocarbonylamino group, a 4-cyanophenylaminocarbonylamino group, an N-ethylethoxycarbonylamino group, an N-methyldodecylsulfonylamino group, an N-(2-cyanoethyl)-p-toluenesulfonylamino group, a hexadecylsulfonylamino group and a trimethylammonio group), a substituted or unsubstituted sulfamoyl group (e.g., a dimethylsulfamoyl group, a hexadecylsulfamoyl group, a sulfamoyl group, a methyloctadecylsulfamoyl group, a methylhexadecylsulfamoyl group, a 2-cyanoethylhexadecylsulfamoyl group, a phenylsulfamoyl group, an N-(3,4-dimethylphenyl)-N-octylsulfamoyl group, a dibutylsulfamoyl group, a dioctadecylsulfamoyl group and a bis(2-methoxycarbonylethylsulfamoyl group), a substituted or unsubstituted acyloxy group (e g., an acetoxy group, a benzoyloxy group, a decyloyloxy group and a chloroacetoxy group), and a substituted or unsubstituted sulfonyloxy group (e.g., a methylsulfonyloxy group, a p-toluenesulfonyloxy group and a p-chlorophenylsulfonyloxy group).

In general formula (B), $U_{n''}$ represents atomic group(s) necessary for forming sequential groups such as $-Y_1-Y_2-Y_3-Y_4$ wherein $U_{n''}$ is $U_4$. Groups of $U_{n''}$ may be the same or different and each represents

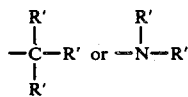

wherein R' represents a bond (a σ-bond or a π-bond) or a substituent represented by R in general formula (A). In general formula (B), plural R' substituents are selected such that the total of Hammett substituent constants $\sigma_p$ is at least about +0.09, preferably at least about +0.3, and more preferably at least about +0.45.

Specific examples of EAG include an aryl group substituted by at least one electronegative group (e.g., a 4-nitrophenyl group, a 2-nitro-4-N-methyl-N-octadecylsulfamoylphenyl group, a 2-N,N-dimethylsulfamoyl-4-nitrophenyl group, a 2-cyano-4-octadecylsulfonylphenyl group, a 2,4-dinitrophenyl group, a 2,4,6-tricyanophenyl group, a 2-nitro-4-N-methyl-N-octadecylcarbamoylphenyl group, a 2-nitro-5-octylthiophenyl group, a 2,4-dimethanesulfonylphenyl group, a 3,5-dinitrophenyl group, a 2-chloro-4-nitro-5-methylphenyl group, a 2-nitro-3,5-dimethyl-4-tetradecylsulfonylphenyl group, a 2,4-dinitronaphthyl group, a 2-ethylcarbamoyl-4-nitrophenyl group, a 2,4-bisdodecylsulfonyl-5-trifluoromethylphenyl group, a 2,3,4,5,6-pentafluorophenyl group, a 2-acetyl-4-nitrophenyl group, a 2,4-diacetylphenyl group and a 2-nitro-4-trifluoromethylphenyl group), a substituted or unsubstituted heterocyclic ring group (e.g., a 2-pyridyl group, a 2-pyrazinyl group, a 5-nitro-2-pyridyl group, a 5-N-hexadecylcarbamoyl-2-pyridyl group, a 4-pyridyl group, a 3,5-dicyano-2-pyridyl group, a 5-dodecylsulfonyl-2-pyridyl group, a 5-cyano-2-pyrazinyl group, a 4-nitro- thiophen-2-yl group, a 5-nitro-1,2-dimethylimidazol-4-yl group, a 3,5-diacetyl-2-pyridyl group and a 1-dodecyl-5-carbamoylpyridinium-2-yl group), a substituted or unsubstituted quinone (e.g., a 1,4-benzoquinon-2-yl group, a 3,5,6-trimethyl-1,4-benzoquinon-2-yl group, a 3-methyl-1,4-naphthoquinon-2-yl group, a 3,6-dimethyl-5-hexadecylthio-1,4-benzoquinon-2-yl group and a 5-pentadecyl-1,2-benzoquinon-4-yl group) or their vinylogs as well as a nitroalkyl group (e.g., a 2-nitro-2-propyl group), a nitroalkenyl group (e.g., a 2-nitroethenyl group) and a monovalent α-diketo compound (e.g., a 2-oxopropanoyl group).

As described above, $R^3$ in formula (II) represents a group of atoms required to form a 3- to 8-membered heterocyclic ring together with the nitrogen atom and the oxygen atom, and some examples of these heterocyclic rings are given below:

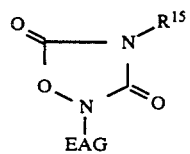

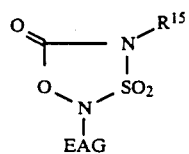

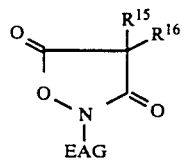

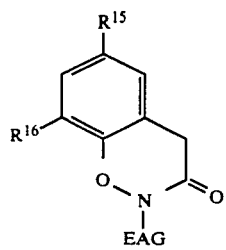

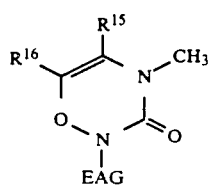

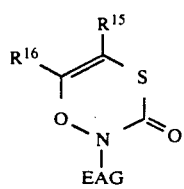

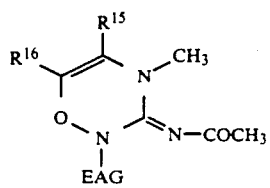

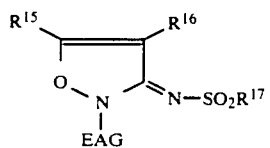

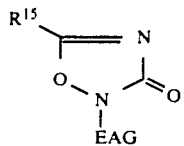

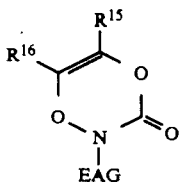

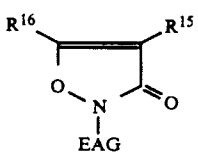

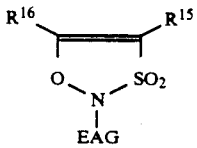

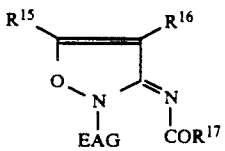

wherein $R^{15}$, $R^{16}$ and $R^{17}$, which may be the same or different, each represents a hydrogen atom, an liphatic group, an aromatic group, a heterocyclic group, having 0 to 40 carbon atoms, preferably 0 to 20 carbon atoms, or a group -(Time)$_t$DIG.

Of compounds represented by general formula (II), examples of positive-forming type compounds that exhibit satisfactory characteristics include compounds represented by the following general formula (III):

$$A''\text{-(Time)}_t\text{DIG.} \qquad \text{(III)}$$

wherein A" represents

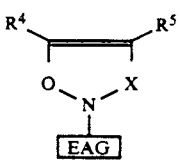

linked to -(Time)$_t$DIG through at least one of $R^4$, $R^5$ and EAG; and EAG, Time, t and DIG have the same meaning as in general formula (II); X represents a divalent linking group, and is preferably a group

or $-SO_2-$; and $R^4$ and $R^5$, which may be the same or different, each represents a hydrogen atom or a substituent, provided that two substituent groups $R^4$ and $R^5$ may be linked to form a saturated or unsaturated carbon ring or heterocyclic ring.

Preferred examples of $R^4$ are a hydrogen atom, a substituted or unsubstituted alkyl group (e.g., a methyl group, an ethyl group, a t-butyl group, an octadecyl group, a phenethyl group and a carboxymethyl group), a substituted or unsubstituted aryl group (e.g., a phenyl group, a 3-nitrophenyl group, a 4-methoxyphenyl group, a 4-acetylaminophenyl group, a 4-methanesulfonylphenyl group, a 2,4-dimethylphenyl group, a 4-tetradecyloxyphenyl group, a group

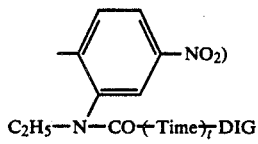

and a substituted or unsubstituted heterocyclic ring group (e.g., a 2-pyridyl group, a 2-furyl group and a 3-pyridyl group).

Preferred examples of $R^5$ are a hydrogen atom, a substituted or unsubstituted alkyl group (e.g., a methyl group, a hydroxymethyl group and a group —CH$_2$—(Time)$_t$DIG), a substituted or unsubstituted aryl group (e.g., a phenyl group, a 4-chlorophenyl group, a 2-methylphenyl group, a group

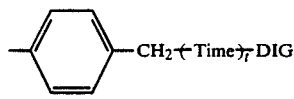

and a group

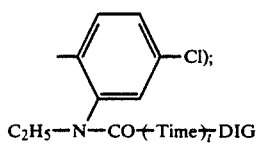

and a substituted or unsubstituted heterocyclic ring group (e.g., a 4-pyridyl group).

Examples of condensed rings formed by $R^4$ and $R^5$ when linked together are given below (the entire condensed ring is shown):

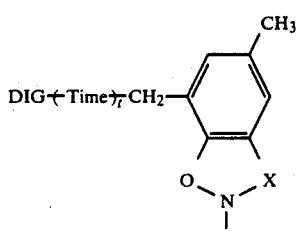

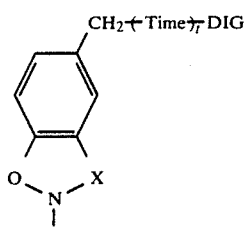

-continued

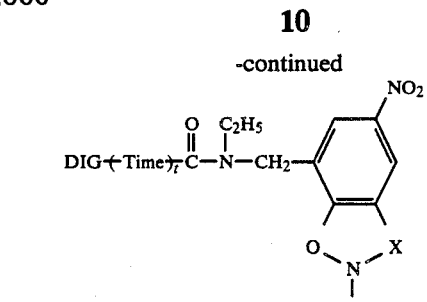

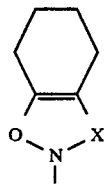

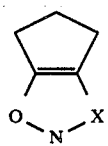

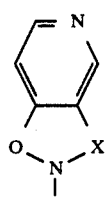

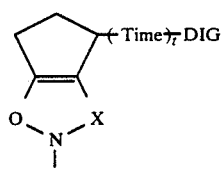

Now, —(Time)$_t$DIG is described in detail below.

Time represents a group that will release the DIG through a subsequent reaction triggered by the cleavage of the nitrogen-oxygen single bond in general formula (I).

Preferred groups represented by Time are represented by the following general formulae (T-1) to (T-4) and (T-10) wherein (*) shows the position through which the group linked to the A moiety of general formula (I) and (*)(*) shows the position where the group is linked to DIG of general formula (I).

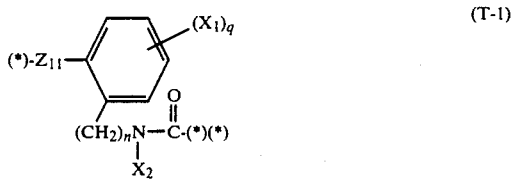

(T-1)

wherein $Z_{11}$ represents (*)—O—,

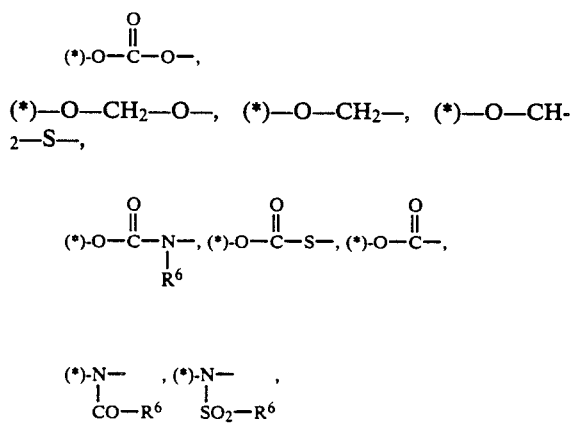

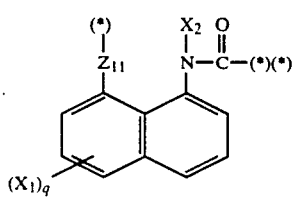

(*)—S—, wherein R⁶ represents a hydrogen atom, an aliphatic group, an aromatic group or a heterocyclic ring group preferably those having 1 to 20 carbon atoms;

X₁ represents a hydrogen atom, an aliphatic group, an aromatic group, a heterocyclic group, —O—R⁷, —SR⁷,

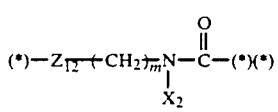

—CO—R⁷, —SO₂R⁷, —SO₂—R⁷, a cyano group, a halogen atom (e.g., fluorine, chlorine, bromine and iodine), or a nitro group, wherein R⁷ and R⁸ may be the same or different and have the same definition as R⁶;

X₂ has the same definition as R⁶;

q is an integer of 1 to 4, provided that when q is 2 or more, the plural substituents represented by X₁ may be the same or different, and plural X₁ groups may be linked to form a ring; and n is 0, 1 or 2.

Groups represented by general formula (T-1) are described, for example, in U.S. Pat. No. 4,248,962.

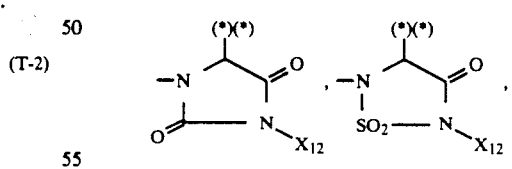

wherein Z₁₁, X₁, X₂ and q each has the same definition as in general formula (T-1)

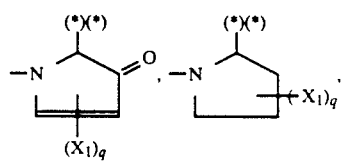

wherein Z₁₂ represents (*)—O—,

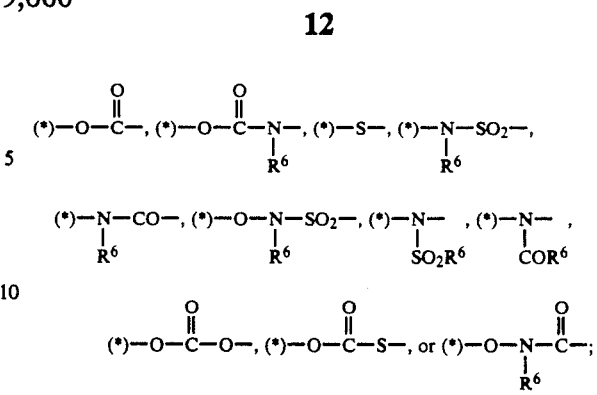

m is an integer of 1 to 4, preferably 1, 2 or 3; and

R⁶ and X₂ have the same definition as in general formula (T-1);

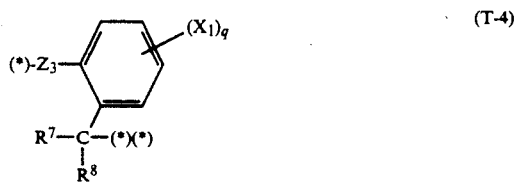

wherein Z₃ represents (*)—O—,

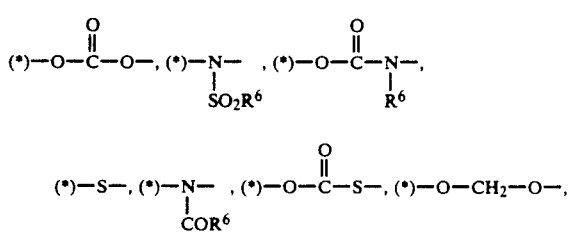

or (*)—O—CH₂—S—; and

R⁶, R⁷, R⁸, X₁ and q have the same definition as those defined in general formula (T-1).

Groups represented by general formula (T-4) are timing groups described, for example, in U.S. Pat. No. 4,409,332.

Preferred heterocyclic ring in formula (T-4) are those shown below.

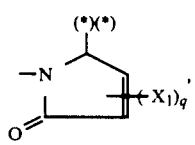

-continued

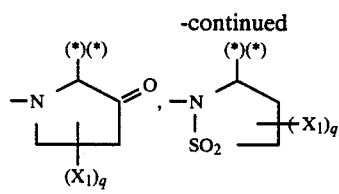

wherein $X_1$ and q have the same definition as in general formula (T-1); and $X_{12}$ represents a hydrogen atom, an aliphatic group, an aromatic group, an acyl group, a sulfonyl group, an alkoxycarbonyl group, a sulfamoyl group, a heterocyclic ring group or a carbamoyl group.

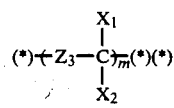  (T-10)

wherein $X_1$ and $X_2$ have the same definition as in general formula (T-1); $Z_3$ has the same definition as in general formula (T-4); and m is an integer of 1 to 4, and is preferably 1 or 2.

In general formulae (T-1) to (T-4) and (T-10), when $X_1$, $X_2$, $R^6$, $R^7$ and $R^8$ represent an aliphatic group, preferably the aliphatic group is one having 1 to 20 carbon atoms, and may be saturated or unsaturated, substituted or unsubstituted, or linear or cyclic or branched. When $X_1$, $X_2$, $R^6 R^7$, and $R^8$ represent an aromatic group, the aromatic group is one having 6 to 20 carbon atoms, preferably 6 to 10 carbon atoms, and is more preferably a substituted or unsubstituted phenyl group. When $X_1$, $X_2$, $R^6$, $R^7$, and $R^8$ represent a heterocyclic ring group, the heterocyclic group is a 5- or 6-membered heterocyclic ring containing as hetero atom at least one nitrogen atom, oxygen atom or sulfur atom, and preferred examples of the heterocyclic ring are a pyridyl group, a furyl group, a thienyl group, a triazolyl group, an imidazolyl group, a pyrazolyl group, a thiazolyl group, an oxadiazolyl group or a pyrrolidinyl group.

Preferred examples of the timing groups are shown below:

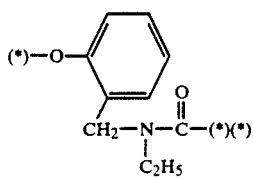 (1)

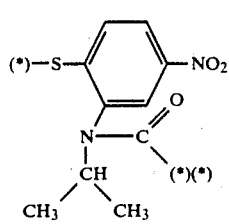 (2)

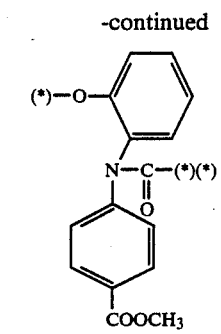 (3)

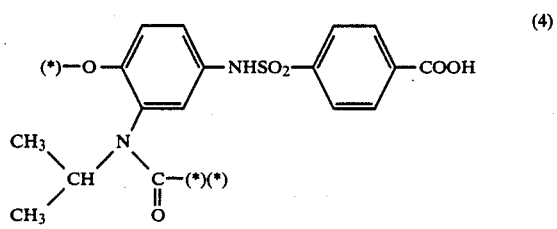 (4)

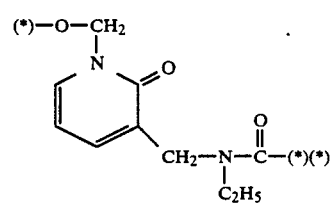 (5)

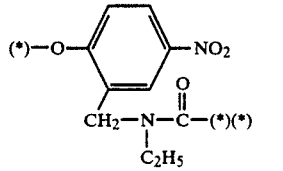 (6)

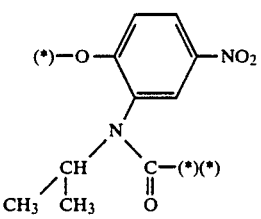 (7)

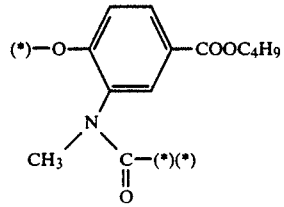 (8)

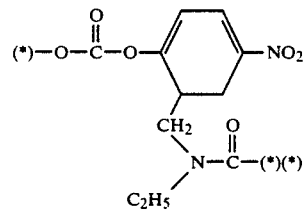 (9)

-continued
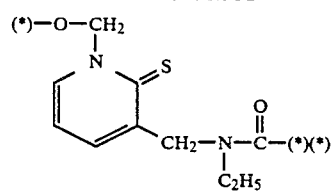 (10)
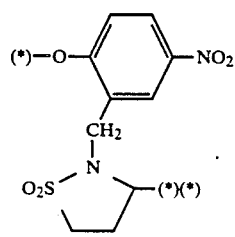 (11)
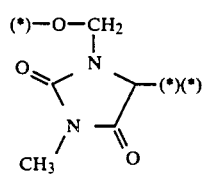 (12)
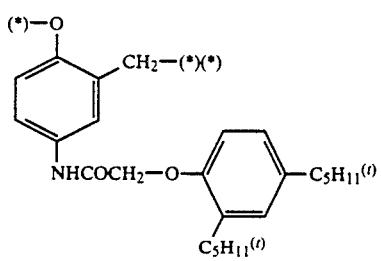 (13)
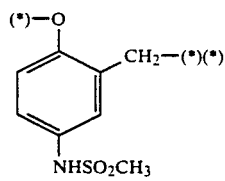 (14)
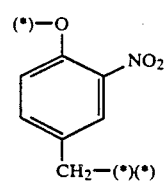 (15)
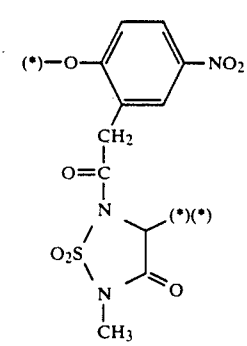 (16)
-continued
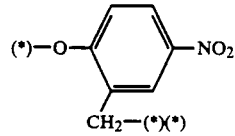 (17)
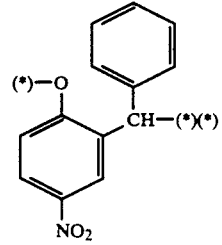 (18)
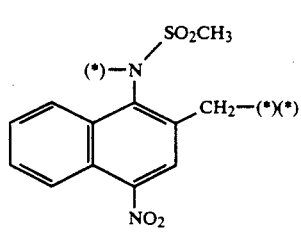 (19)
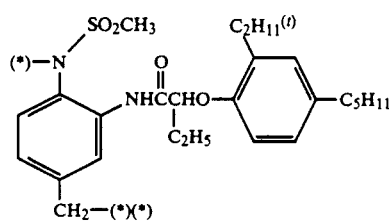 (20)
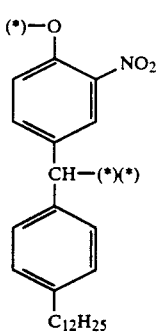 (21)
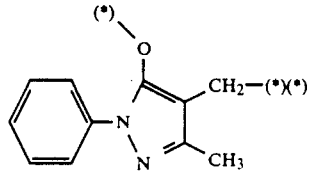 (22)
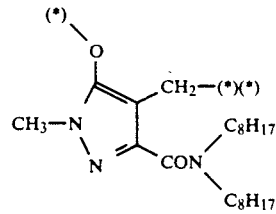 (23)

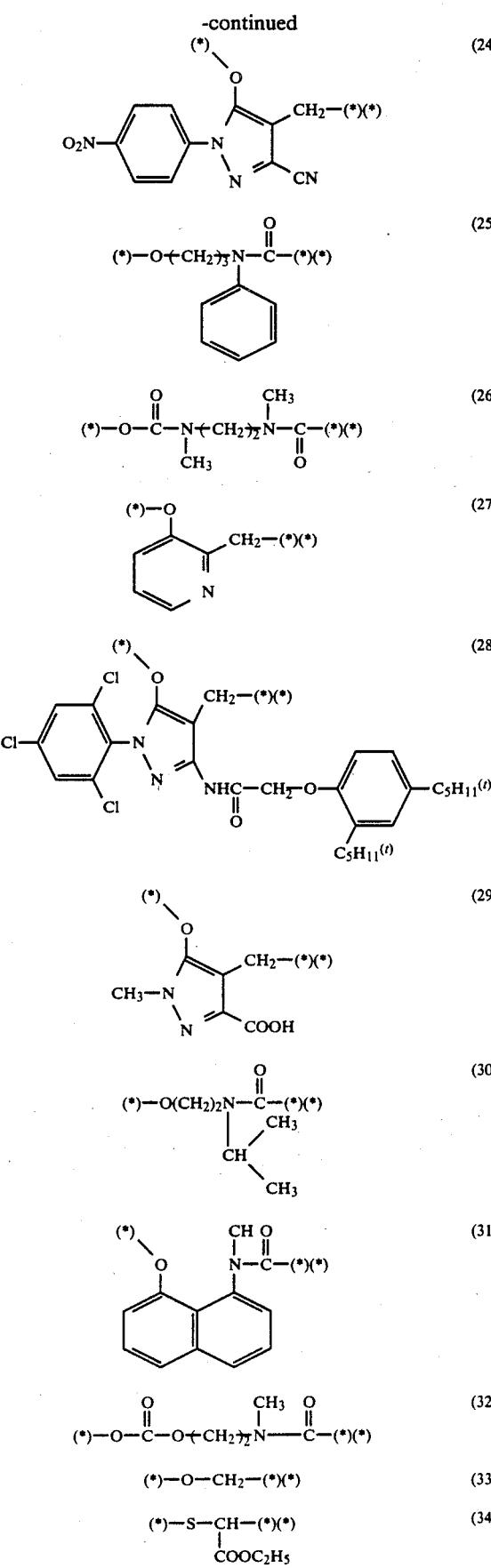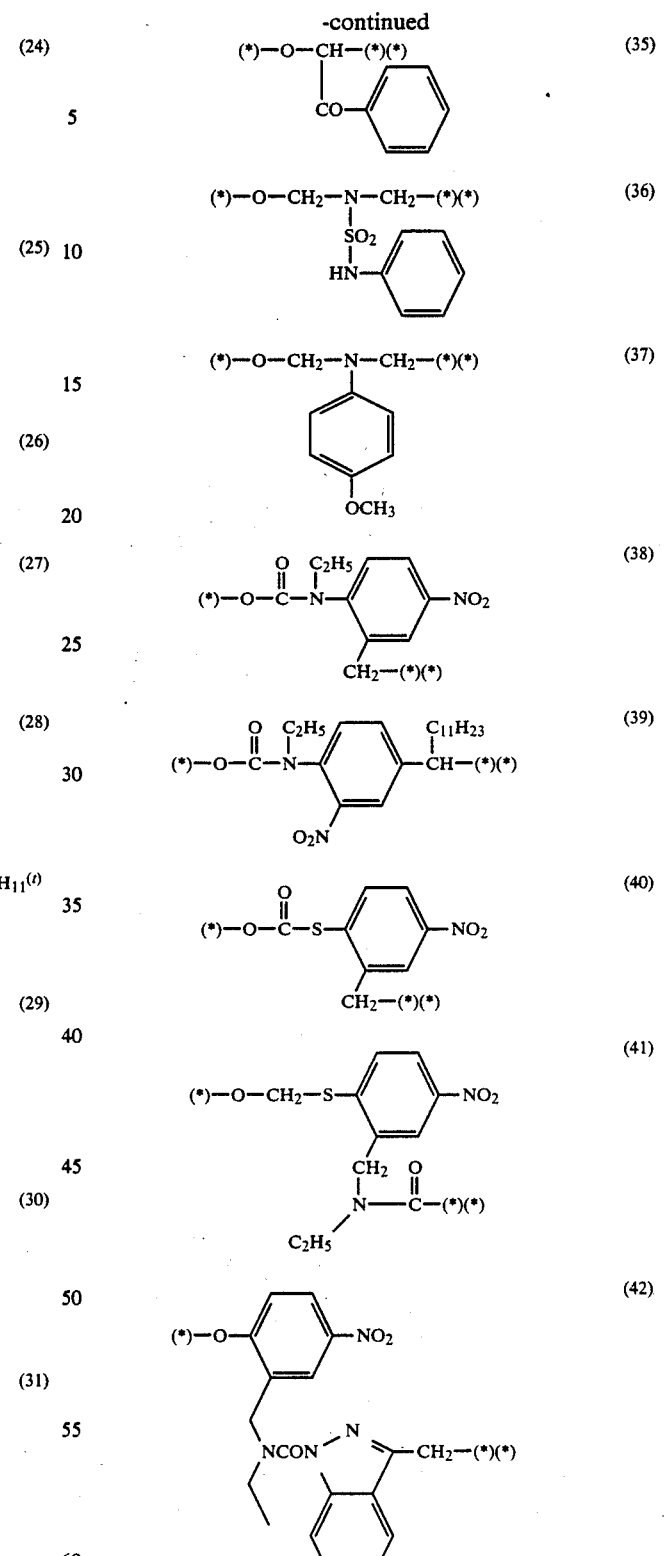
Preferably the layer which contains the compound represented by general formula (I) is a silver halide emulsion layer or a layer adjacent thereto, with the latter being particularly preferred because of advantages of excellent shelf life of film, etc. If there are color photosensitive layers comprising at least three or more silver halide emulsion layers, it is advantageous to use at least one compound (I) in combination with each emulsion layer or a corresponding layer adjacent thereto, so that emulsion layers that have been spectrally sensitized individually can be controlled differently (depending on the colors). Compound (I) of the present invention may be used in an amount of from $1\times10^{-8}$ mol/m$^2$ to $1\times10^{-2}$ mol/m$^2$, preferably from $1\times10^{-7}$ mol/m$^2$ to $1\times10^{-3}$ mol/m$^2$.

In the present invention, compound (I) is used in combination with a reducing material. The reducing material may previously be coated in any one of the layers on the base, may be contained in a layer on another base or may be contained in a processing liquid (an alkaline processing composition). In any case, the reducing material is used by bringing the reducing material into in contact with compound (I) to reduce the compound (I). There is no particular restriction on the type and the amount of the reducing material, and any reducing material can be used if it can reduce the compound (I).

Reducing materials preferably include hydroquinones, aminophenols, aminonaphthols, 3-pyrazolidinones, saccharin, and their precursors, picoliniums and compounds described in Japanese Patent Application (OPI) No. 110827/78 as electron donors.

Examples of such reducing materials are given below:

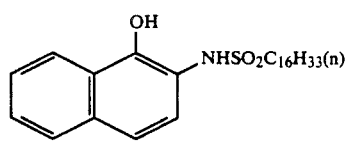
S-1

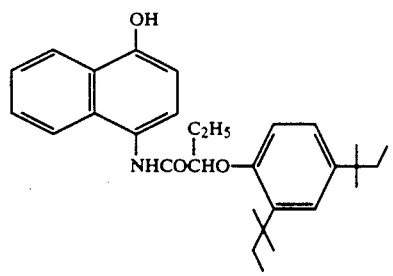
S-2

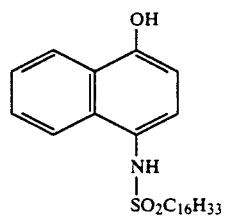
S-3

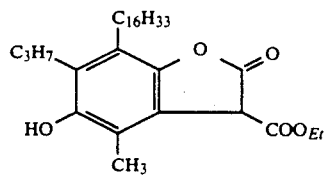
S-4

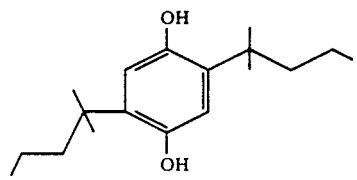
S-5

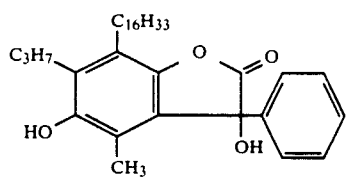
S-6

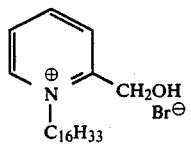 S-7
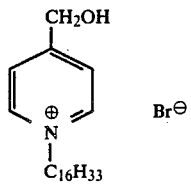 S-8
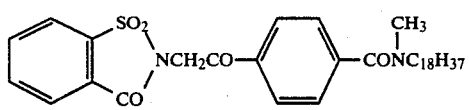 S-9
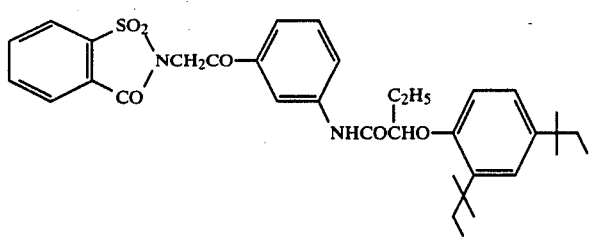 S-10
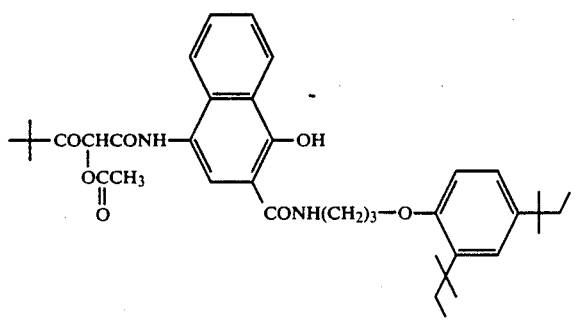 S-11
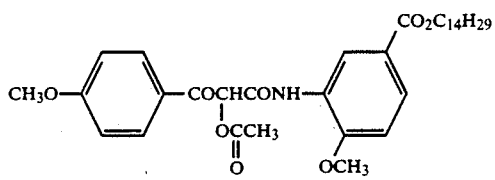 S-12
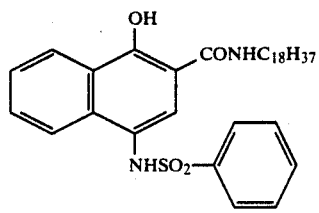 S-13
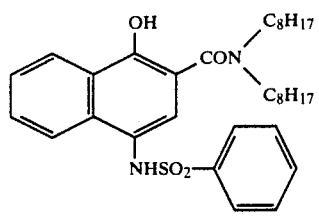 S-14

-continued
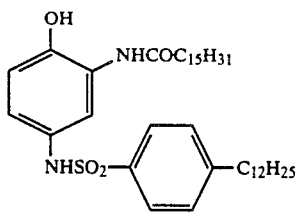 S-15
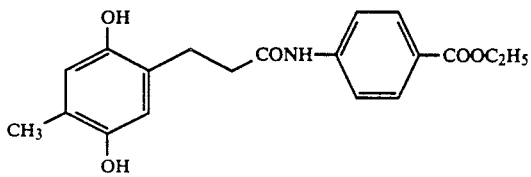 S-16
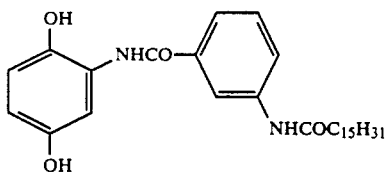 S-17
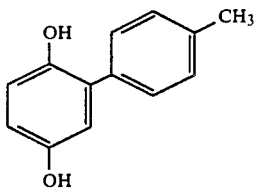 S-18
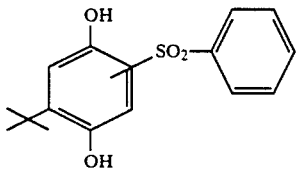 S-19
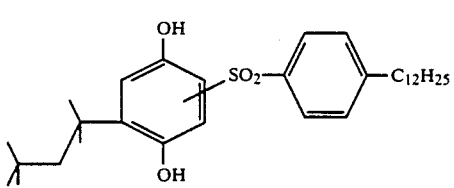 S-20
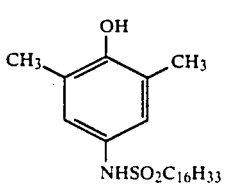 S-21
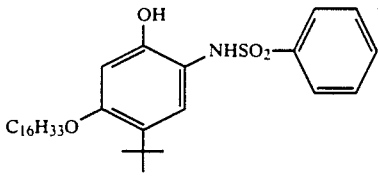 S-22

-continued
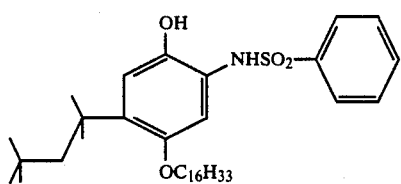
S-23
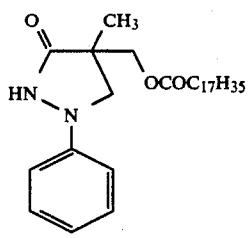
S-24
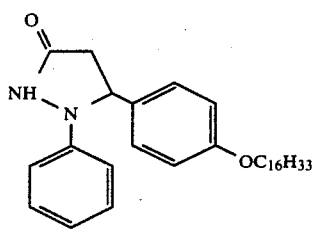
S-25
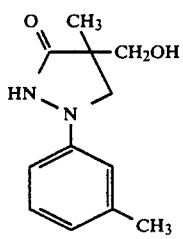
S-26
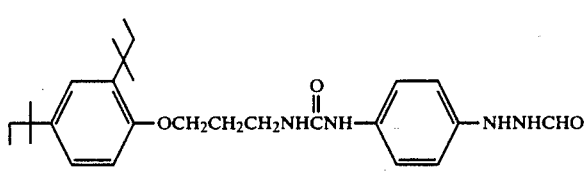
S-27
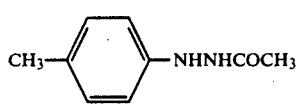
S-28
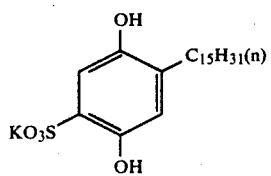
S-29
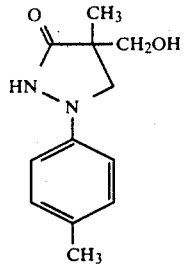
S-30

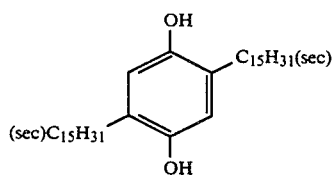

S-31

In the present invention, when a reducing material to reduce a compound (I) is contained in a layer on the same base, it is preferred that they are positioned in the same layer or adjacent layers.

Reducing materials that can be contained in a processing liquid include usual developing agents, hydroquinones, and reducing materials that can be dissolved in alkalis such as inorganic reducing agents. Although many of these reducing materials are used for other functions, in many cases, in the present invention they can also be used to function as reducing materials. For example, a developing agent such as a phenidone derivative has the function of the cross oxidation of a dye donating redox compound from silver development and also can act as a reducing material for a compound (I) of the invention Specific examples of compounds represented by general formula (I) are given below, but the present invention is not to be construed as being limited thereto.

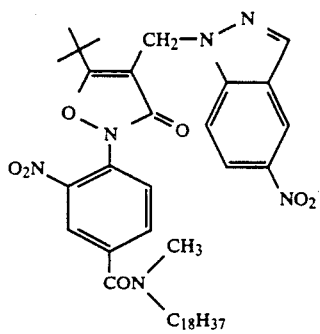

1

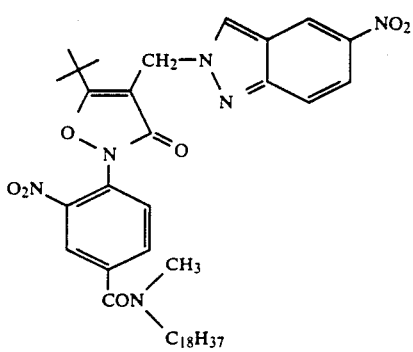

2

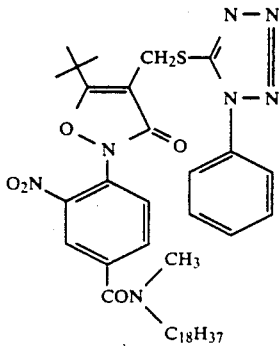

3

-continued
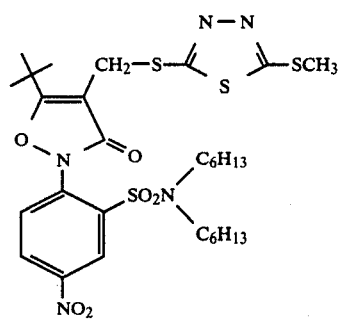
4
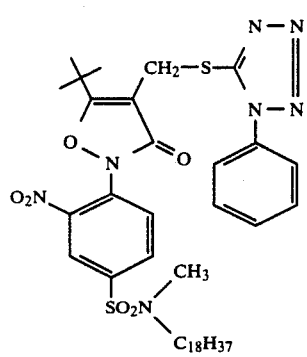
5
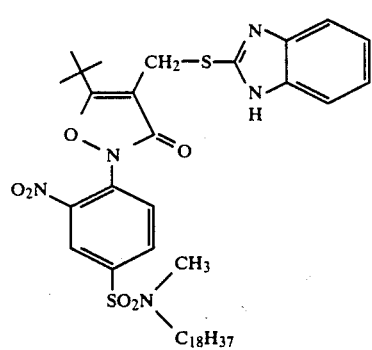
6
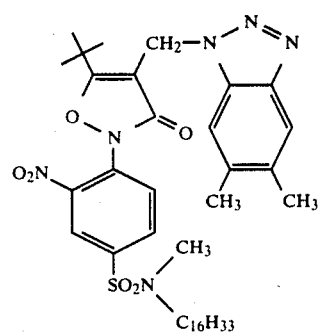
7

-continued
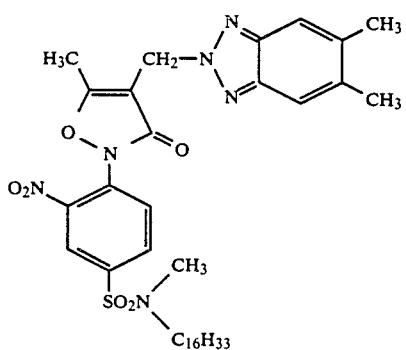
8
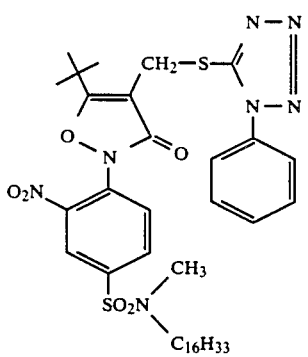
9
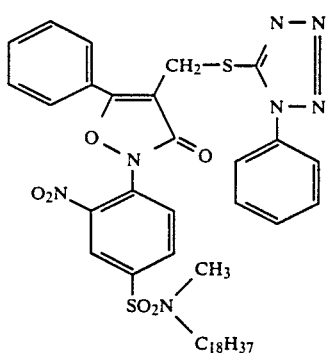
10
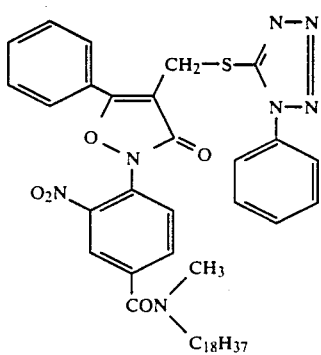
11

-continued
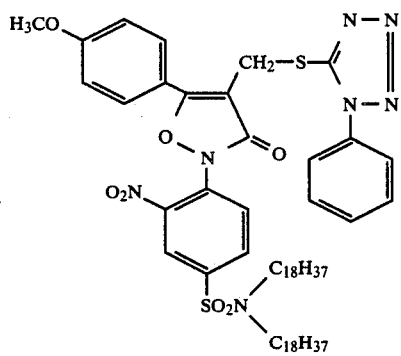
12
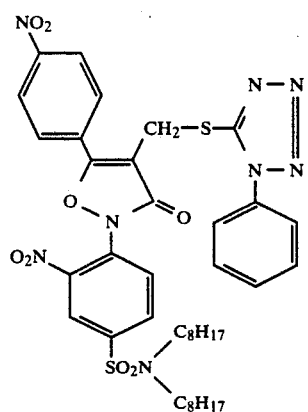
13
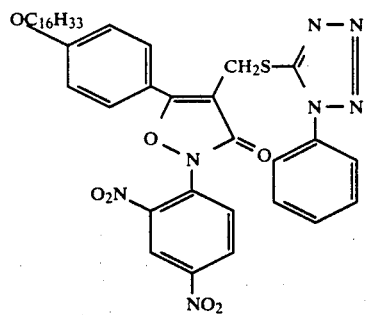
14
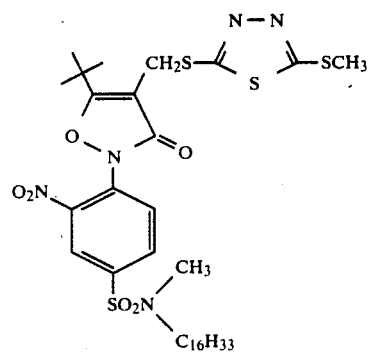
15

-continued
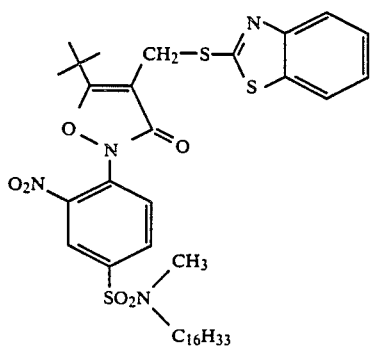
16
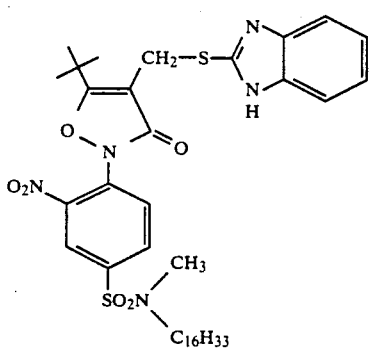
17
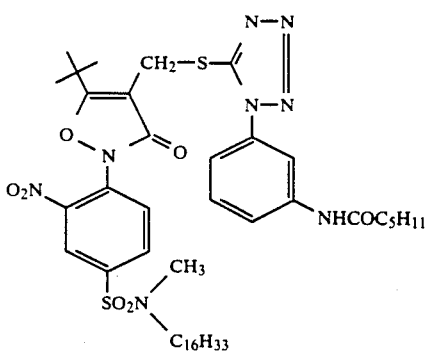
18
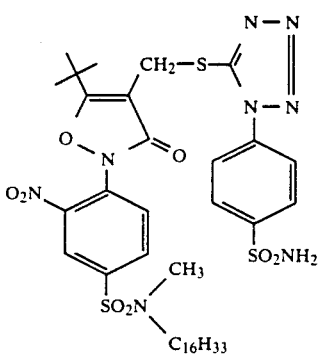
19

-continued
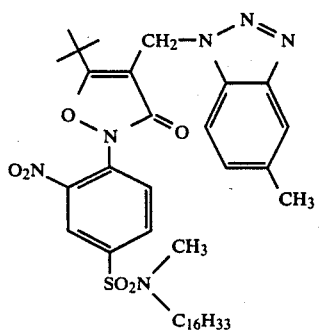
20
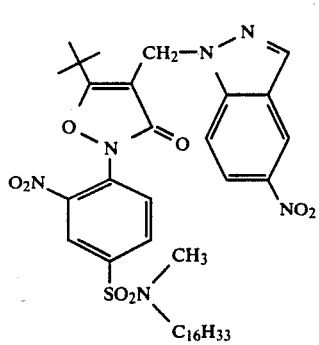
21
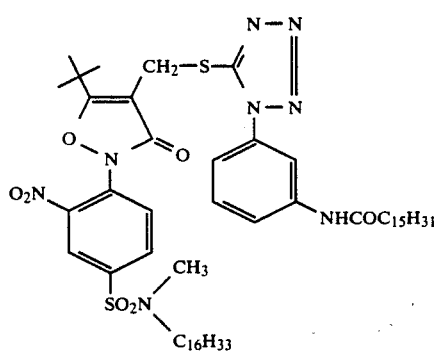
22
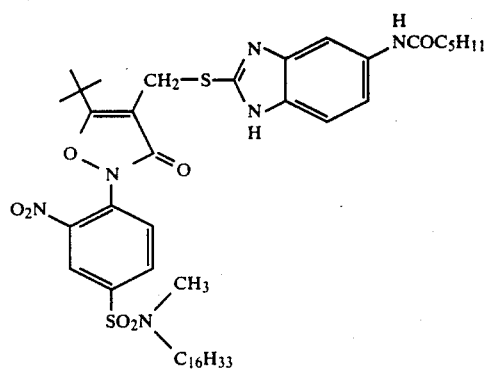
23

-continued

24

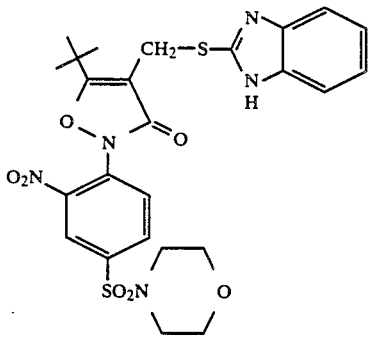

25

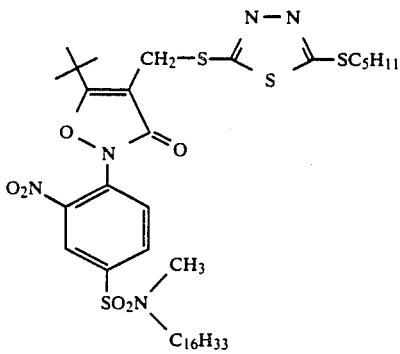

With respect to the synthesis of the compounds of the present invention, the most important factor is the process of joining the nitrogen-oxygen group and the electron-accepting group. This process can generally be divided into two methods: (1) a method wherein a nitro group is introduced to the electron-accepting portion, that is then reduced in a zinc-ammonium chloride system to be converted into hydroxylamine, and (Time)$_t$. DIG is joined, and (2) a method wherein a group that can be easily replaced such as a halogen atom is introduced to the electron-accepting portion followed by its nucleophilic replacement with hydroxylamine or its equivalent. With respect to the first method, the synthesis process described in S. R. Sandler & W. Karo, *Organic Functional Group Preparations* is possible. With respect to the second method, a reaction can be accompoished in ethanol, dimethylformamide or dimethyl sulfoxide under neutral or basic conditions. To make the present invention clear, specific synthesis examples are illustrated below.

SYNTHESIS EXAMPLE 1

Synthesis of 5-t-Butyl-3-hydroxyisoxazole 583.7 g of hydroxylamine hydrochloride was dissolved in 2 liters of a 4N aqueous sodium hydroxide solution, then 2 liters of ethanol was added while cooling with ice, and the pH of the solution was adjusted to 10.0 by adding a 4N aqueous sodium chloride solution-/ethanol (1:1) solution mixture. To the solution simultanelusly were added dropwise 1,380 g of ethyl pivaloylacetate and a 4N aqueous sodium hydroxide water/ethanol (1:1) solution to maintain the pH of the reaction solution at 10±0.2 and the temperature at 0° to 5° C.

After the completion of the dropwise addition, the reaction mixture was stirred for 2 hours at room temperature, and after 6 kg of concentrated hydrochloric acid at 0° C. was added thereto, the reaction mixture was allowed to stand for 12 hours. The deposited crystals were filtered, washed with water and dried.

The yield was 770 g (68.2% of theoretical yield) and the melting point was 99° to 101° C.

SYNTHESIS EXAMPLE 2

Synthesis of 4-Chloro-3-nitro-N-methyl-N-hexadecylbenzenesulfonamide

Synthesis Example 2-1

Synthesis of 4-Chloro-3-nitrobenzenesulfonyl Chloride

To a solution mixture of 1,280 g of potassium 4-chloro-3-nitrobenzenesulfonate in 1,150 ml of acetonitrile, 250 ml of sulfolane and 30 ml of dimethylacetamide was added dropwise 1,250 ml of phosphorus oxychloride while the temperature was kept at 60° to 70° C. After the reaction proceeded for 3 hours at 73° C., the reaction mixture was cooled with water, then 400 ml of water was added thereto gradually, and then 5 liters of ice water was poured into the reaction mixture. The deposited crystals were filtered followed by washing with water and drying.

The yield was 1,060 g (84% of theoretical yield) and the melting point was 55° to 56° C.

Synthesis Example 2—2

Synthesis of 4-Chloro-3-nitro-N-hexadecylbenzenesulfonamide 1 liter of dichloromethane was added to 800 g of 4-chloro-3-nitrobenzenesulfonyl chloride and the solution was cooled to 0° C. To the solution was added dropwise a mixture of 600 g of hexadecylamine, 251 ml of triethylamine and 780 ml of dichloromethane at 20° to 30° C. After the reaction mixture was reacted for 2 hours at room temperature, the dichloromethane was distilled off under reduced pressure, and 3 liters of methanol was added to the residue followed by heating to dissolve it. The solution was cooled gradually and after crystals were precipitated at room temperature, 3 liters of methanol was added thereto to further facilitate the crystallization under cooling with ice water, and the crystals were filtered and dried.

The yield was 1,020 g (88% of theoretical yield) and the melting point was 91° to 93° C.

Synthesis Example 2-3

Synthesis of 4-Chloro-3-nitro-N-methyl-N-hexadecylbenzenesulfonamide 170 g of 4-chloro-3-nitro-N-hexadecylbenzenesulfonamide was dissolved in 640 ml of acetone, then 79 g of potassium carbonate, 6 ml of polyethylene glycol 400 and 71 g of dimethyl sulfate were added and the reaction mixture was heated for 5 hours under reflux. 240 ml of acetone was added thereto, then 870 ml of water was added dropwise at 40° C., and when the reaction mixture was cooled to room temperature, crystals precipitated out. The crystals were filtered, washed with water and then with methanol and dried.

The yield was 169 g (97% of theoretical yield) and the melting point was 74° to 75° C.

SYNTHESIS EXAMPLE 3

Synthesis of Compound 9

Synthesis Example 3-1

Synthesis of 5-t-Butyl-2-(4-N-methyl-N-hexadecylsulfamoyl-2-nitrophenyl)-3-isoxazolone 470 g of 4-chloro-3-nitro-N-hexadecylbenzenesulfonamide synthesized in Synthesis Example 2-3, 169 g of 5-t-butyl-3-hydroxyisoxazole synthesized in Synthesis Example 1, 168 g of potassium carbonate, and 1.2 liters of dimethyl sulfoxide were mixed and reacted at 65° C. for 6 hours.

Then, ice water was poured into the reaction liquid, and the precipitated crystals were filtered, washed with water and then dried.

The yield was 576 g (100% of theoretical yield) and the melting point was 67° to 68° C.

Synthesis Example 3-2

Synthesis of 5-t-Butyl-4-chloromethyl-2-(4-N-methyl-N-hexadecylsulfamoyl-2-nitrophenyl)-3-isoxazolone 550 g of 5-t-butyl-2-(4-N-methyl-N-hexadecylsulfamoyl-2-nitrophenyl)-3-isoxazolone, 200 g of zinc chloride, 200 g of paraformaldehyde and 1.5 liters of acetic acid were mixed, and the mixture was heated under reflux for 10 hours while hydrogen chloride gas was passed therethrough. After cooling, the reaction mixture was poured into water, and the preicpitated crystals were filtered and recrystallized from an acetonitrile/methanol (1:4) solvent mixture.

The yield was 585 g (96% of theoretical yield) and the melting point was 56° C.

Synthesis Example 3—3

Synthesis of Compound 9

250 g of 5-t-butyl-4-chloromethyl-2-(2-N-methyl-N-hexadecylsulfamoyl-2-nitrophenyl)-3-isoxazolone and 75 g of 1-phenyl-5-mercaptotetrazole were dissolved in 500 ml of acetone, then 60 g of potassium carbonate and 5 g of sodium iodide were added thereto, and the reaction mixture was stirred for 2 hours at room temperature. Then, aqueous dilute hydrochloric acid was poured into the reaction mixture, extraction with ethyl acetate was carried out, and the extract was washed with water, dried and condensed under reduced pressure. 1 liter of ethanol and 100 m( of ethyl acetate were added to the residue to effect recrystallization.

The yield was 250 g (82% of theoretical yield) and the melting point was 73° to 75° C.

SYNTHESIS EXAMPLE 4

Synthesis of Compound 10

Synthesis Example 4-1

Synthesis of 5-Phenyl-3-hydroxyisoxazole 200 ml of water and 300 ml of ethanol were added to 40 g of sodium hydroxide to dissolve the sodium hydroxide. 69.5 g of hydroxylamine hydrochloride was added thereto, and the pH of the solution was adjusted to 10.0 by adding a 2N sodium hydrochloride ethanol/water (3:2) solution mixture. Under cooling with ice, 192 g of ethyl benzoylacetate and a 2N sodium hydroxide in ethanol/water (3:2) solution mixture were added dropwise simultaneously to the reaction solution so that the pH of the reaction solution was 10±0.3. After completion of the addition and stirring for 3 hours at room temperature, the reaction mixture was poured to a mixture of 500 g of concentrated hydrochloric acid and 500 g of ice, then 2.5 liters of ethanol was added to the reaction mixture and after the reaction mixture was heated for 3 hours under reflux, 2 liters of water was added thereto followed by cooling. The precipitated crystals were filtered, washed with water and dried.

The yield was 98 g (61% of theoretical yield) and the melting point was 150° to 151° C.

Synthesis Example 4-2

Synthesis of 4-Chloro-3-nitro-N-methyl-N-octadecylbenzenesulfonamide 300 m( of chloroform was added to 100 g of 4-chloro-3-nitrobenzenesulfonyl chloride and the mixture was cooled to 0° C. Then, a chloroform solution containing 84.3 g of methyloctadecylamine was added dropwise to the mixture. After 39.5 g of triethylamine was added dropwise thereto while the temperature was kept at 0° to 10° C.., the mixture was stirred for 1 hour at room temperature. The chloroform was distilled off under reduced pressure, then 500 ml of methanol was added to the residue, and it was heated to dissolve the residue. The mixture was cooled to precipitate crystals and the crystals were filtered and dried.

The yield was 109 g (71% of theoretical yield) and the melting point was 86° to 87° C.

Synthesis Example 4-3

Synthesis of Compound 10

The compound was synthesized in the manner shown in Synthesis Example 3—3 from the compound synthesized in Synthesis Example 3-1.

The melting point was 117° to 118° C.

SYNTHESIS EXAMPLE 5

Synthesis of Compound 3

Synthesis Example 5-1

Synthesis of
4-Chloro-3-nitro-N-methyl-N-octadecylbenzamide 105.7 g of 3-nitro-4-chlorobenzoic acid and 800 ml of acetonitrile were mixed, then 68.6 g of thionyl chloride was added thereto, and the mixture was heated for 4 hours under reflux After cooling, the solvent was distilled off, and the reaction mixture was dissolved in chloroform. Then, 63.5 g of triethylamine was added to the resulting solution, and the temperature was brought to 5° C. Then, 148.6 g of N-methyloctadecylamine in chloroform was added dropwise to it. After completion of the reaction, water was added, and the organic phase was separated and dried over anhydrous sodium sulfate. After the inorganic material was filtered off, the solvent was distilled off, and recrystallization from acetonitrile/methanol (1:3) was effected The yield was 186 g (76.0% of theoretical yield) and the melting point was 55° to 56° C.

Synthesis Example 5-2

Synthesis of
5-t-Butyl-2-(4-N-methyl-N-octadecylcarbamoyl-2-nitrophenyl)-3-isoxazolone 300 ml of dimethylformamide was added to 34.1 g of N-methyl-N-octadecyl-3-nitro-4-chlorobenzamide, 12.4 g of 5-t-butyl-3-hydroxyisoxazole and 12.4 g of potassium carbonate, and the reaction was carried out at 100° C. for 5 hours. The solvent was distilled off under reduced pressure, ethyl acetate and water were added to the reaction mixture, then after they were stirred, the organic phase was separated and the main product was purified by silica gel column chromatography, and recrystallized from n-hexane/ethyl acetate.

The yield was 18.9 g (43.1% of theoretical yield) and the melting point was 64° C.

Synthesis Example 5-3

Synthesis of
4-Chloromethyl-5-t-butyl-2-(4-N-methyl-N-octadecylcarbamoyl-2-nitrophenyl)-3-isoxazolone 36 g of 5-t-butyl-2-(4-N-methyl-N-octadecylcarbamoyl-2-nitrophenyl)-3-isoxazolone, 5.7 g of paraformaldehyde and 10.3 g of zinc chloride were mixed with 250 ml of acetic acid, and the reaction was effected for 20 hours at 100° C. while hydrogen chloride gas was passed therethrough. After completion of the reaction, the reaction mixture was cooled and poured to ice water. The deposited solid was filtered, dissolved in chloroform, and purified by column chromatography.

The yield was 10.0 g (26% of theoretical yield) and the melting point was 77° C.

Synthesis Example 5-4

Synthesis of Compound 3

40 g of 4-chloromethyl-5-t-butyl-2-(4-N-methyl-N-octadecylcarbamoyl-2-nitrophenyl)-3-isoxazolone and 12 g of 1-phenyl-5-mercaptotetrazole were dissolved in acetone. Then, 14 g of potassium carbonate was added to the solution, and the mixture was stirred for 3 hours at room temperature. After the inorganic material was filtered off, recrystallization from methanol was effected.

The yield was 33 g (67% of theoretical yield) and the melting point was 66° to 68° C.

The silver halide emulsion used in the present invention is a hydrophilic colloidal dispersion of silver chloride, silver bromide, silver chlorobromide, silver bromoiodide or silver bromochloroiodide or a mixture thereof, and although the halogen composition is selected depending on the application of the photosensitive material and the processing conditions, silver bromide, silver bromoiodide or silver bromochloroiodide wherein the iodide content is about 10 mol % or below and the chloride content is about 30 mol % or below is particularly preferred.

In the present invention, a negative type emulsion for forming a surface latent image or a direct reversal type emulsion can be used. The latter emulsions include an internal latent image type emulsion and a prefogged direct reversal type emulsion In the present invention, internal latent image type silver halide emulsions are used advantageously, including emulsions containing different metals, core/shell type emulsions and conversion type emulsions described, for example, in U.S. Pat. Nos. 2,592,250, 3,206,313, 3,447,927, 3,761,276 and 3,935,014.

Typical nucleators for emulsions of this type include hydrazines described in U.S. Pat. Nos. 2,588,982 and 2,563,785; hydrazones and hydrazides described in U.S. Pat. No. 3,227,552; quaternary salt compounds described in British Patent No. 1,283,835, Japanese Patent Publication No. 38164/74, and U.S. Pat. Nos. 3,734,738, 3,719,494 and 3,615,615; sensitizing dyes having a nucleating substituent with an antifogging effect in the dye molecule described in U.S. Pat. No. 3,718,470; and acylhydrazinophenyl thiourea compounds described in U.S. Pat. Nos. 4,030,925 and 4,031,127.

The silver halide emulsion used in the present invention can have a color sensitivity increased by a spectral sensitizing dye, if desired, including cyanine dyes, merocyanine dyes, etc.

Of dye-releasing redox (hereinafter "DRR") compounds, compounds capable of releasing a dye when their oxidized form is hydrolyzed under alkaline conditions are described, for example, in U.S. Pat. Nos. 4,053,312, 4,055,428, 4,076,529, 4,152,153 and 4,135,929, Japanese Patent Application (OPI) Nos. 149328/78 (corresponding to U.S. Pat. No. 4,268,625), 104343/76 (corresponding to U.S. Pat. No. 4,198,235), 46730/78 (corresponding to U.S. Pat. No. 4,179,291), 130122/79 (corresponding to U.S. Pat. No. 4,273,855), 3819/78 (corresponding to U.S. Pat. No. 4,149,892), 12642/81, 16130/81 and 16131/81 (corresponding to U.S. Pat. No. 4,336,322).

Of these, DRR compounds that can release yellow dyes are described, for example, in U.S Pat. No. 4,013,633, Japanese Patent Application (OPI) Nos. 149328/78 (corresponding to U.S. Pat. No. 4,268,625), Nos. 114930/76 and 71072/81 and *Research Disclosure*, No 17630 (1978) and No. 16475 (1977); those that can release magenta dyes are described, for example, in U.S. Pat. Nos. 3,954,476, 3,931,144 and 3,932,308, Japanese Patent Application (OPI) Nos. 23628/78, 106727/77 (corresponding to U.S. Pat. No. 4,493,855), 65034/79 (corresponding to U.S. Pat. No. 4,233,237), 161332/79 (corresponding to U.S. Pat. No. 4,255,509), 4028/80 (corresponding to U.S. Pat. No. 4,250,246), 36804/80, 73057/81, 71060/81 and 134850/80 and West German Patent Application (OLS) No. 2,847,371; and those that can release cyan dyes are described, for example, in U.S. Pat. Nos. 3,942,987, 3,929,760 and 4,013,635 and Japanese Patent Application (OPI) Nos. 109928/76

(corresponding to U.S. Pat. No. 4,013,635), 8827/77, 143323/78, 47823/78 and 71061/81.

Redox compounds capable of releasing a dye by a ring closing reaction or the like in the unoxidized state include those described, for example, in U.S. Pat. Nos. 4,139,379 and 3,980,479, West German Patent Application (OLS) Nos. 2,402,900 and 2,448,811.

In the present invention, dye-releasing redox compounds represented by the general formula $Y-(L)_s X$ are preferred, wherein Y represents a redox nucleus (carrier), X represents a dye-forming group or a dye-forming precursor group, L represents a divalent linking group selected from the group consisting of an alkylene group (or an alkylidene group) having 1 to 6 carbon atoms, an arylene group and a heterocyclic ring group connected either directly to X or through —O—, —S—, —SO$_2$—, or

$-\overset{|}{N}R^{10}$, in which $R^{10}$ represents a hydrogen atom, an alkyl group, —CO—, —CONH— or —SO$_2$NH—, and s is an integer of 0 to 2.

The above dye residue may be a residue of any type of dye, provided that the dye residue has sufficient diffusibility that the dye residue can pass through the photographic layer in the photographic material to reach the image-receiving layer.

For this purpose, if desired, the dye residue may have one or more substituent groups rendering it water-soluble. Examples of suitable water-soluble groups are a carboxyl group, a sulfo group, a sulfonamido group, a sulfamoyl group and an aliphatic or aromatic hydroxyl group.

Dyes particularly suitable in the present invention are azo dyes, azomethine dyes, anthraquinone dyes, phthalocyanine dyes, indigoid dyes, triphenylmethane dyes, metal complex dyes and colored metal complexes.

The term "dye precursor residue" means a residue of a compound that can be converted into a dye by the release of an auxochrome in a color development system upon oxidation (i.e., the addition of a released auxochrome to the chromophore) in usual processing steps during photographic processing or in additional processing steps. In this case, the dye procursors may be leuco dyes or dyes that can be converted to other dyes during photographic processing.

Examples of Y effective for the redox compounds are N-substituted sulfamoyl groups. Examples of suitable Y groups include those represented by the following formula (Y—I):

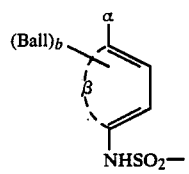

(Y-I)

wherein β represents a nonmetallic atomic group required to form a substituted or unsubstituted benzene ring, which benzene ring may have a carbon ring or a heterocyclic ring condensed thereto to form, for example, a naphthalene ring, a quinoline ring, a 5,6,7,8-tetrahydronaphthalene ring or a chroman ring, each of which may be substituted by a halogen atom, an alkyl group, an alkoxy group, an aryl group, an aryloxy group, a nitro group, an amino group, an alkylamino group, an arylamino group, an amido group, a cyano group, an alkylmercapto group, a keto group, a carboxyl group, a heterocyclic ring group, or the like;

α represents a group represented by OG$^1$ or —NHG$^2$ in which G$^1$ represents a hydrogen atom or a group that can be hydrolyzed to a hydroxyl group, and preferably a hydrogen atom, a group

or a group

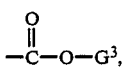

in which G$^3$ represents an alkyl group, particularly an alkyl group having 1 to 18 carbon atoms, such as a methyl group, an ethyl group or a propyl group, a halogensubstituted alkyl group having 1 to 18 carbon atoms, such as a chloromethyl group or a trifluoromethyl group, a phenyl group or a substituted phenyl group; G$^2$ represents a hydrogen atom, an alkyl group having 1 to 22 carbon atoms, or a hydrolyzable group, preferably a hydrolyzable group represented by

—SO$_2$G$^5$ or —SOG$^5$, in which G$^4$ represents an alkyl group having 1 to 4 carbon atoms (such as a methyl group), a halogen-substituted alkyl group (such as a mono-, di- or trichloromethyl group or a trifluoromethyl group), an alkylcarbonyl group (such as an acetyl group), an alkoxy group, a substituted phenyl group (such as a nitrophenyl group or a cyanophenyl group), a phenoxy group optionally substituted by a lower alkyl group or a halogen atom, a carboxyl group, an alkoxycarbonyl group, an aryloxycarbonyl group, an alkylsulfonylethoxy group or an arylsulfonylethoxy group; and G$^5$ represents a substituted or unsubstituted alkyl group or aryl group;

b is an integer of 0, 1 or 2, preferably 1 or 2, most preferably 1, when unless α contains an alkyl group that renders the compound represented by general formula (Y—I) immobile and nondiffusible and α represents a group represented by —OG$^1$ or α represents —NG$^2$ and G$^2$ represents a hydrogen atom, an alkyl group having 1 to 8 carbon atoms or a hydrolyzable group; and Ball represents a ballasting group that renders the compound nondiffusible.

Specific examples of such a (Y—I) group are described in Japanese Patent Application (OPI) Nos. 33826/73 (corresponding to U.S. Pat. No. 3,928,312), 50736/78, 54021/79 (corresponding to U.S. Pat. No. 4,135,929) and 143230/79 (corresponding to U.S. Pat. No. 4,258,120).

Other suitable examples of Y include a group represented by the following formula (Y—II):

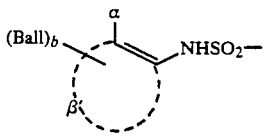

(Y-II)

wherein Ball, α and b have the same meaning as defined in general formula (Y—I), β' represents an atomic group required to form a substituted or unsubstituted carbon ring such as a benzene ring, which benzene ring may have a carbon ring or a heterocyclic ring condensed thereto to form, for example, a naphthalene ring, a quinoline ring, a 5,6,7,8-tetrahydronaphthalene ring or a chroman ring, each of which may be substituted by a halogen atom, an alkyl group, an alkoxy group, an aryl group, an aryloxy group, a nitro group, an amino group, an alkylamino group, an arylamino group, an amido group, a cyano group, an alkylmercapto group, a keto group, a carboxyl group, a heterocyclic ring group, or the like. Specific examples of (Y—II) are described, for example, in Japanese Patent Application (OPI) Nos. 113624/76 (corresponding to U.S. Pat. No. 4,055,428), 149328/78 (corresponding to U.S. Pat. No. 4,268,625), 65034/79 (corresponding to U.S. Pat. No. 4,233,237), 111344/79 (corresponding to U.S. Pat. No. 4,245,028) and 16131/81 (corresponding to U.S. Pat. No. 4,336,322) and U.S. Pat. No. 4,053,312.

In the present invention, dye-releasing redox compounds that are obtained by replacing DIG in general formula (I) by DYE (dye part) can also be used.

The coating amount of the dye-releasing redox compound is about $1 \times 10^{-4}$ to $1 \times 10^{-2}$ mol/m$^2$, preferably about $2 \times 10^{-4}$ to $2 \times 10^{-3}$ mol/m$^2$.

The dye-releasing redox compound used in the present invention can be dispersed into a hydrophilic colloid that is a carrier in various ways depending on the type of the compound. For example, a compound having a dissociative group such as a sulfo group and a carboxyl group can be dispersed by dissolving it in water or an aqueous alkaline solution and adding the resulting solution to a hydrophilic colloid solution. On the other hand, compounds sparingly soluble in aqueous media but readily soluble in organic solvents can be dispersed by methods well known in the art.

The color diffusion transfer photographic element used in the present invention can be used in any film unit in which photosensitive silver halide photographic emulsions, dye-releasing redox compounds and a dye-receiving layer are carried on the same base.

In a typical film unit on one transparent base are coated silver halide photographic emulsion layers containing dye-releasing redox compounds and a dye image-receiving layer, and it is not required to peel off the image-receiving layer, etc., after the transferred image is completed. More specifically, the film unit contains at least one dye image-receiving layer and in a preferred embodiment, a combination of a blue-sensitive silver halide emulsion layer, a green-sensitive silver halide emulsion layer and a red-sensitive silver halide emulsion layer; a combination of a green-sensitive emulsion layer, a red-sensitive emulsion layer and an infrared-sensitive emulsion layer; or a combination of a blue-sensitive emulsion layer, a red-sensitive emulsion layer and an infrared-sensitive emulsion layer. These layers contain a yellow dye-providing material, a magenta dye-providing material and a cyan dye-providing material, respectively (herein the term "infrared-sensitive emulsion layer" means an emulsion layer sensitive to light having a wavelength of 700 nm or over, particularly 740 nm or over). A white reflective layer containing a solid pigment such as titanium oxide is provided between the image-receiving layer and the silver halide layers or the dye-releasing redox compound-containing layers so that the transferred image can be appreciated through the transparent base. To make it possible to complete development processing in daylight, a light screening layer may be placed between the white reflective layer and the photosensitive silver halide layer. Further, to enable all or part of the photosensitive element to be released from the image-receiving element when required, a release layer may be provided in a suitable place (as described, for example, in Japanese Patent Application (OPI) No. 67840/81 and Canadian Patent No. 674,082).

In a non-peel-apart unit, the photosensitive element is coated on one transparent base, a white reflective layer is coated thereon, and an image-receiving layer is placed thereon. A peel-apart unit, in which an image-receiving element, a white reflective layer, a release layer and a photosensitive element are coated on the same base, and the photosensitive element can be intentionally released from the image-receiving element, is disclosed in U.S. Pat. No. 3,730,718.

The present invention includes a color diffusion transfer photographic film unit in which the photographic film contains a photosensitive element having on a white base at least (a) a dye image-receiving layer, (b) a release layer, and (c) at least one silver halide emulsion layer containing a dye-releasing redox compound, an alkali processing composition containing an opacifying agent and a transparent cover sheet.

When a development inhibitor-releasing compound represented by represented by compound (I) or (II) according to the invention was used in a small amount, a photographic material excellent in fog prevention (i.e., Dmin) could be attained without reducing the rate of development speed. Since compound (I) releases an inhibitor in inverse relation to the development of a silver halide emulsion, i.e., basically releases the inhibitor in an undeveloped part (fogged part) without releasing it in a developed part, the development in the image areas where development is required is fast, because the development of that part is not restrained. Since the development in the fogged area is restrained effectively, the fogging can be lowered substantially. In comparison with the prior development inhibitors that work uniformly throughout the surface, irrespective of the silver development pattern, and, therefore, reduce the development rate, the present development inhibitor-releasing compounds act only in areas where they are required and, therefore, are ideal compounds.

The present compounds are reduced by a reducing material that is also present during processing, so that the nitrogen-oxygen bond is cleaved and a development inhibitor is released through the subsequent electron transfer. Since the amount of the reducing material present is lowered in image areas where silver development occurs sufficiently, the reduction does not occur to release the development inhibitor.

The invention is now illustrated in greater detail with reference to specific embodiments thereof, but the present invention is not to be construed as being limited thereto. Unless otherwise indicated, all parts, percents and ratios are by weight.

EXAMPLE 1

Multilayer integral color diffusion transfer photosensitive sheets and a cover sheet were prepared as follows.

Preparation of Photosensitive Sheets

Each of Photosensitive Sheets 1 to 9 was prepared by applying the following layers (1) to (13) in that order on a polyethylene terephthalate transparent base.

(1) An image-receiving layer containing 3.0 g of copoly(styrene-N-vinylbenzyl-N-methyl-piperidinium chloride) and 3.0 g of gelatin per m².
(2) A white reflective layer containing 20 g of titanium dioxide and 20 g of gelatin per m².
(3) A light-screening layer containing 2.0 g of carbon black and 1.5 g of gelatin per m².
(4) A layer containing 0.44 g of a cyan dye-releasing redox compound shown below, 0.09 g of tricy-

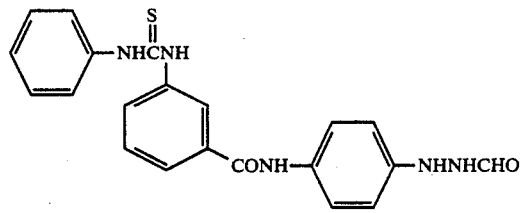

(6) A layer containing 0.43 g of 2,5-di-t-pentadecyl-hydroquinone, 0.1 g of trihexyl phosphate and 0.4 g of gelatin per m².
(7) A layer containing 0.3 g of a magenta dye-releasing redox compound shown below, 0.08 g of tricyclohexyl phosphate, 0.009 g of 2,5-di-tert-pentadecylhydroquinone and 0.5 g of gelatin per m².

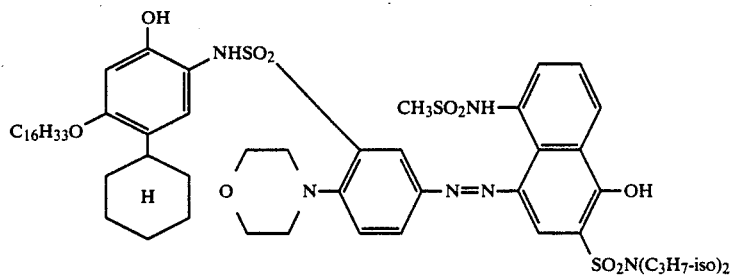

clohexyl phosphate, 0.008 g of 2,5-di-t-pentadecyl-hydroquinone and 0.8 g of gelatin per m².

(8) A green-sensitive emulsion layer containing a green-sensitive internal latent image type direct

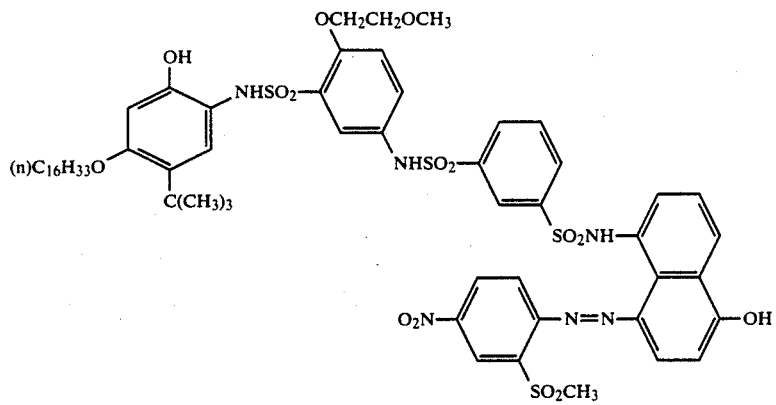

(5) A red-sensitive emulsion layer containing a red-sensitive internal latent image type direct positive silver bromide emulsion in an amount of 1.03 g/m² in terms of silver (silver bromide grains having octahedral form and 1.7 μm of grain size), 1.2 g of gelatin, 0.04 mg of a nucleator shown below and 0.13 g of 2-sulfo-5-n-pentadecylhydroquinone sodium salt per m².

positive silver bromide emulsion in an amount of 0.82 g/m² in terms of silver (silver bromide grain having an octahedral form and 1.7 μm of grain size), 0.9 g of gelatin, 0.03 g of the same nucleator as used in Layer (5) and 0.08 g of 2-sulfo-5-n-pentadecylhydroquinone sodium salt.

(9) The same layer as Layer (6).
(10) A layer containing 0.53 g of a yellow dye-releasing redox compound having the structure shown below, 0.13 g of tricyclohexyl phosphate, 0.014 g of 2,5-di-t-pentadecylhydroquinone and 0.7 g of gelatin.

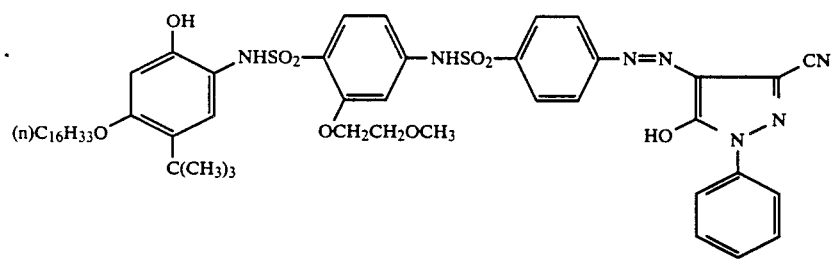

(11) A blue-sensitive emulsion layer containing a blue-sensitive internal latent image type direct positive silver bromide emulsion in an amount of 1.09 g/m² in terms of silver (silver bromide grain having an octahedral form and 1.7 μm of grain size), gelatin (1.1 g/m²), the same nucleator as used in Layer (5) (0.04 mg/m²), 2-sulfo-5-n-pentadecylhydroquinone sodium salt (0.07 g/m²) and each compound shown in Table 1 in an amount shown in Table 1.

(12) An ultraviolet absorbing layer containing ultraviolet absorbing agents having the structures shown below (each in an amount of $4 \times 10^{-4}$ mol/m²) and gelatin (0.30 g/m²).

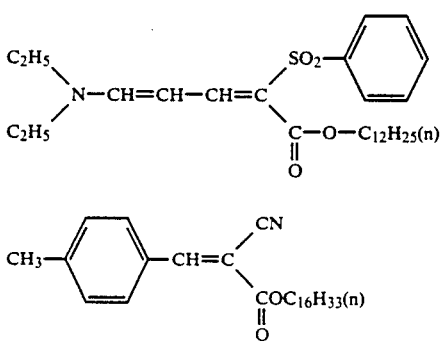

(13) A protective layer containing polymethyl methacrylate (0.10 g/m², average grain size: 4 μm), gelatin (0.8 g/m²) and, as a hardening agent, triacryloyltriazine (0.02 g/m²).

Constitution of Cover Sheet A

A cover sheet was prepared by applying the following layers (1') to (4') successively on a transparent polyethylene terephthalate base.

(1') A neutralizing layer containing an acrylic acid/butyl acrylate (weight ratio: 8:2) copolymer with an average molecular weight of 50,000 (10 g/m²), and 1,4-bis(2,3-epoxypropoxy)butane (0.2 g/m²).

(2') A second timing layer containing cellulose acetate (acetylation degree: 51.0%) and methyl vinyl ether/maleic acid monomethyl ester alternating copolymer in a weight ratio of 95/5, in an amount of 7.5 g/m².

(3') An auxiliary neutralizing layer containing methyl vinyl ether/maleic anhydride alternating copolymer (1.05 g/m²) and 5-(2-cyano-1-methylthio)-1-phenyltetrazole (0.98 mmol/m²).

(4') A first timing layer having a thickness of 2 μm formed by mixing a styrene/n-butyl acrylate/acrylic acid/N-methylolacrylamide copolymer latex (49.7:42.3:3:5) and a methyl methacrylate/acrylic acid/N-methylolacrylamide copolymer latex (weight ratio: 4:3) such that the solids weight ratio of the former latex to the latter latex was 6 to 4.

| Composition of Processing Liquid A | |
|---|---|
| 1-p-Tolyl-4-hydroxymehyl-4-methyl-3-pyrazolidone | 14 g |
| Methylhydroquinone | 0.3 g |
| 5-Methylbenzotriazole | 3.5 g |
| Sodium Sulfite (anhydride) | 0.2 g |
| Carboxymethyl Cellulose Na Salt | 58 g |
| Potassium Hydroxide (28% aq. soln.) | 200 cc |
| Benzyl Alcohol | 1.5 cc |
| Carbon Black | 150 g |
| Water | 685 cc |

After the thus-prepared Photosensitive Sheets 1 to 9 were exposed to light through a continuous optical wedge, they were each superposed with Cover Sheet A, and Processing Liquid A was uniformly distributed therebetween by passing the assembly between a pair of press rolls at a temperature of 35° C. to be developed. After 1 hour, each of the color densities was measured by a color densitometer, and Dmax and Dmin shown in Table 1 were obtained.

Immediately after development, the change in Dmax was measured every 5 seconds, and the time required to reach ½ of the density (Dmax) after 60 minutes was read, to determine the rate of dye transfer. A high rate of transfer means satisfactory.

As is apparent from Table 1, the photographic elements using the present photosensitive sheets were excellent, in that Dmin was greatly reduced without reducing Dmax or dye transfer rate.

It is considered from other analytical experiments that the difference in the rate of dye transfer corresponded to the difference in the rate of silver development. That is, a slow rate of dye transfer is due to a slow silver development rate.

TABLE 1

| Sample No. | Compound | Amount (mol/m²) | Dmax | Dmin | Dye Transfer Rate (T₅₀ %) (sec) | Remarks |
|---|---|---|---|---|---|---|
| 1 | — | — | 1.83 | 0.32 | 110 | Comparison |
| 2 | Comparative | $1.0 \times 10^{-5}$ | 1.82 | 0.31 | 115 | " |

TABLE 1-continued

| Sample No. | Compound | Amount (mol/m²) | B Dmax | Dmin | Dye Transfer Rate (T₅₀ %) (sec) | Remarks |
|---|---|---|---|---|---|---|
| 3 | Comparative Compound A | 5.0 × 10⁻⁵ | 1.79 | 0.28 | 145 | " |
| 4 | Compound 3 | 1.4 × 10⁻⁴ | 1.80 | 0.26 | 110 | Invention |
| 5 | Compound 9 | " | 1.82 | 0.26 | 109 | " |
| 6 | Compound 10 | " | 1.84 | 0.26 | 111 | " |
| 7 | Compound 28 | " | 1.83 | 0.25 | 110 | " |
| 8 | Compound 31 | " | 1.84 | 0.28 | 110 | " |
| 9 | Compound 32 | " | 1.78 | 0.26 | 113 | " |

Comparative Compound A

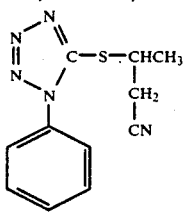

EXAMPLE 2

Each of Photosensitive Sheets 10 to 16 was prepared by applying the following layers successively on a polyethylene terephthalate transparent base.

(1) A layer containing copolymer of divinyl-benzene-vinylbenzyl-N-trihexylammonium chloride (2.0 g/m²) and gelatin (2.8 g/m²).

(2) A layer containing copolymer of styrene-N-vinylbenzyl-N-methylpiperidinium chloride (1.5 g/m²) and gelatin (1.0 g/m²).

(3) A layer that was the same as Layer (2) in Example 1.

(93:4) A layer that was the same as Layer (3) in Example 1.

(5) A layer that was the same as Layer (4) in Example 1.

(6) A layer containing titanium dioxide (2.0 g/m²), gelatin (0.2 g/m²) and the compound shown in Table 2.

(7) A layer that was the same as Layer (5) in Example 1.

(8) A layer that was the same as Layer (6) in Example 1.

(9) A layer that was the same as Layer (7) in Example 1.

(10) A layer containing titanium oxide (1.0 g/m²), gelatin (0.2 g/m²) and the compound shown in Table 2.

(11) A layer that was the same as Layer (8) in Example 1.

(12) A layer that was the same as Layer (9) in Example 1.

(13) A layer containing a yellow dye-releasing redox compound having the structure shown below (0.5 g/m²), tricyclohexyl phosphate (0.13 g/m²) and gelatin (0.5 g/m²)

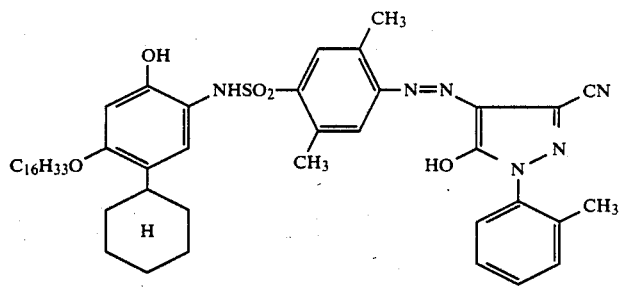

(14) A layer that was the same as Layer (11) in Example 1, without the compound shown in Table 1.

(15) A layer that was the same as Layer (12) in Example 1 with the addition of the compound shown in Table 2.

(16) A layer that was the same as Layer (13) in Example 1.

With respect to the thus-prepared Photosensitive Sheets 10 to 16, Dmax, Dmin and the rate of dye transfer were measured as in Example 1, and the results shown in Table 2 were obtained.

From Table 2 it is understood that the present photographic elements were excellent, in that Dmax was high, Dmin was sufficiently low even when they were processed at high temperatures, and the rate of transfer was high.

TABLE 2

| Example No. | Development Inhibitor-Releasing Compound | | | | Reducing Agent | | | |
|---|---|---|---|---|---|---|---|---|
| | | Layer to Which the Compound Was Added | | | | Layer to Which the Compound Was Added | | |
| | Compound | Layer (6) (mol/m²) | Layer (10) (mol/m²) | Layer (15) (mol/m²) | Compound | Layer (6) (mol/m²) | Layer (10) (mol/m²) | Layer (15) (mol/m²) |
| 0 | — | — | — | — | — | — | — | — |
| 1 | Compound 28 | $3 \times 10^{-4}$ | $7 \times 10^{-4}$ | $1.4 \times 10^{-3}$ | — | — | — | — |
| 2 | " | " | " | " | S-29 | $3 \times 10^{-4}$ | $7 \times 10^{-4}$ | $1.4 \times 10^{-3}$ |
| 3 | " | " | " | " | S-31 | " | " | " |
| 4 | " | " | " | " | S-23 | " | " | " |
| 5 | " | " | " | " | S-1 | " | " | " |
| 6 | " | " | " | " | S-10 | " | " | " |

| Example No. | Dmin at 35° C. | | | Rate of Transfer ($T_{50}$ %) | | | Remarks |
|---|---|---|---|---|---|---|---|
| | R | G | B | R | G | B | |
| 0 | 0.32 | 0.30 | 0.32 | 37 | 65 | 115 | Comparison |
| 1 | 0.30 | 0.28 | 0.28 | 37 | 64 | 115 | Invention |
| 2 | 0.29 | 0.26 | 0.26 | 36 | 65 | 116 | " |
| 3 | 0.29 | 0.26 | 0.26 | 38 | 64 | 118 | " |
| 4 | 0.29 | 0.26 | 0.26 | 37 | 66 | 115 | " |
| 5 | 0.29 | 0.26 | 0.26 | 36 | 65 | 115 | " |
| 6 | 0.29 | 0.26 | 0.26 | 39 | 67 | 115 | " |

EXAMPLE 3

A cover sheet and a processing liquid were prepared as shown below.

Cover Sheet B (1') A layer that was the same as Layer (1') in Example 1.

(2') A layer that was the same as Layer (2') in Example 1.

(3') A layer that was the same as Layer (3') in Example 1, but the amount of the tetrazole derivative was decreased to 0.49 mol/m².

(4') A layer that was the same as Layer (4') in Example 1.

Processing Liquid B

A processing liquid that was the same as Processing Liquid A, except that the amount of 5-methylbenzotriazole was halved.

The thus-prepared photographic sheet, cover sheet and the processing liquid were exposed, superposed and developed as in Example 1, and the results given in Table 3 were obtained.

It can be understood from Table 3 that when a photosensitive sheet containing the present antifoggant reversely imagewise was used, if the amount of development inhibitor precursor in the cover sheet was decreased or the amount of development inhibitor (5-methylbenzotriazole) in the processing liquid was decreased, a significantly reduced Dmin could be attained, and an image with a beautiful white background could be obtained. In addition, when the amount of the inhibitor was decreased in the processing liquid, the rate of dye transfer was significantly increased. That is, when a photosensitive sheet of the present invention and a processing inhibitor containing a reduced amount of development inhibitor were combined, a photographic element low in Dmin and high in dye transfer rate could be obtained.

TABLE 3

| Photo-Sensitive Sheet No. | Cover Sheet | Processing Liquid | Dmin at 35° C. | | | Rate of Transfer $D_B$ ($T_{50}$%) (sec) | Remarks |
|---|---|---|---|---|---|---|---|
| | | | R | G | B | | |
| 10 | A | A | 0.32 | 0.30 | 0.32 | 115 | Comparison |
| 10 | A | B | 0.34 | 0.35 | 0.43 | 98 | " |
| 10 | B | A | 0.38 | 0.32 | 0.35 | 114 | " |
| 12 | A | A | 0.29 | 0.26 | 0.26 | 116 | Invention |
| 12 | B | A | 0.30 | 0.27 | 0.27 | 115 | " |

While the invention has been described in detail and with reference to specific embodiments thereof, it will be apparent to one skilled in the art that various changes and modifications can be made therein without departing from the spirit and scope thereof.

What is claimed:

1. A color diffusion transfer photographic material comprising a base having thereon at least one silver halide emulsion layer and a dye image-receiving layer, at least one layer thereof containing a dye-releasing redox compound and at least one layer thereof containing a development inhibitor-releasing compound represented by the following general formula (I):

$$A\text{-(Time)}_t\text{DIG} \qquad (I)$$

wherein A represents

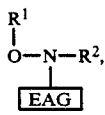

linked to ─(Time)$_t$─DIG through at least one of $R^1$, $R^2$ and EAG; $R^1$ and $R^2$, which may be the same or different, each represents a single bond or a substituent other than a hydrogen atom, provided that $R^1$ and $R^2$ may be linked to form a ring; EAG represents an electron-accepting group; Time represents a group capable of releasing DIG after EAG accepts an electron and the N—O bond is cleaved in A; DIG represents a development inhibitor precursor; and t is an integer of 0 or 1.

2. The color diffusion transfer photographic material as claimed in claim 1, wherein A represents

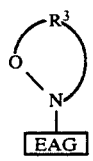

linked to ─(Time)$_t$─DIG through at least one of $R^3$ and EAG; $R^3$ represents an atomic group necessary for forming a 3-membered to 8-membered heterocyclic ring containing said nitrogen atom and said oxygen atom, and EAG has the same definition as in general formula (I).

3. The color diffusion transfer photographic material as claimed in claim 1, wherein said development inhibitor precursor represented by DIG is selected from the group consisting of a substituted or unsubstituted mercaptotriazole, a substituted or unsubstituted mercaptoazaindene, a substituted or unsubstituted mercaptopyrimidine, a substituted or unsubstituted benzotriazole, a substituted or unsubstituted indazole, and a substituted or unsubstituted benzimidazole.

4. The color diffusion transfer photographic material as claimed in claim 1, wherein EAG is represented by the following general formulae (A) or (B):

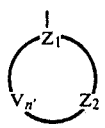 (A)

wherein $Z_1$ represents

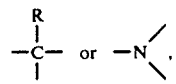

$Z_2$ and V each represents

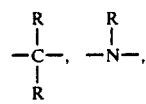

—O—, —S—, or —SO$_2$—, wherein R represents a $\pi$-bond, a hydrogen atom, or a substituent selected from the group consisting of a substituted or unsubstituted alkyl group, a substituted or unsubstituted alkenyl group, a substituted or unsubstituted alkynyl group, a cyano group, a nitro group, a halogen atom, a substituted or unsubstituted heterocyclic ring group, a sulfo group, a carboxyl group, a substituted or unsubstituted aryloxycarbonyl group, a substituted or unsubstituted alkoxycarbonyl group, a substituted or unsubstituted carbamoyl group, a hydroxyl group, a substituted or unsubstituted azo group, a substituted or unsubstituted aryloxy group, a substituted or unsubstituted alkoxy group, a sulfino group, a sulfeno group, a mercapto group, a substituted or unsubstituted acyl group, a substituted or unsubstituted arylthio group, a substituted or unsubstituted alkylthio group, a substituted or unsubstituted aryl group, a substituted or unsubstituted sulfonyl group, a substituted or unsubstituted sulfinyl group, a substituted or unsubstituted amino group, a substituted or unsubstituted sulfamoyl group, a substituted or unsubstituted acyloxy group, and a substituted or unsubstituted sulfonyloxy group; and n' is an integer of 1 to 6, provided that the plural V groups may be the same or different; and

 (B)

wherein U represents

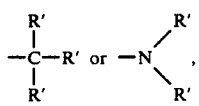

wherein R' represents a $\sigma$-bond, a $\pi$-bond or a substituent represented by R in general formula (A); and n'' is an integer of 1 to 6.

5. The color diffusion transfer photographic material as claimed in claim 4, wherein EAG represents an aryl group substituted with at least one electron-attracting group; a substituted or unsubstituted heterocyclic ring group, a substituted or unsubstituted quinone group, a nitroalkyl group, a nitroalkenyl group, or a monovalent α-diketo group.

6. The color diffusion transfer photographic material as claimed in claim 2, wherein said heterocyclic ring formed by $R^3$ is selected from the group consisting of:

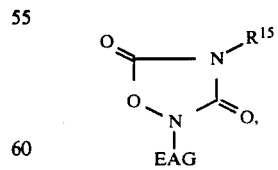

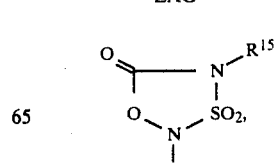

-continued

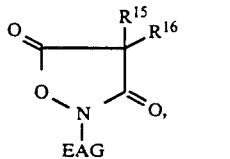

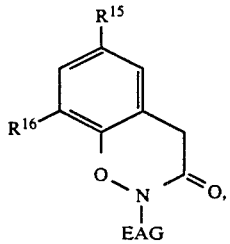

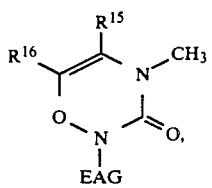

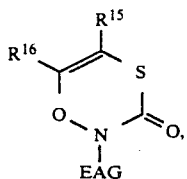

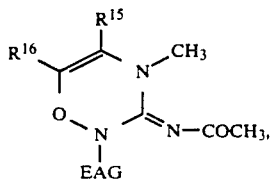

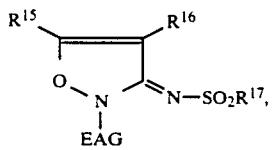

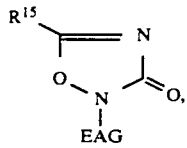

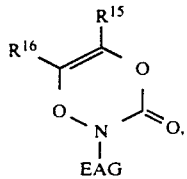

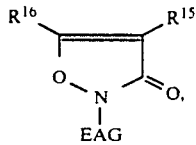

-continued

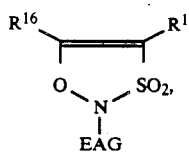

and

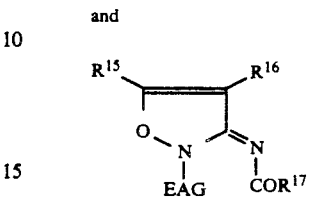

wherein $R^{15}$, $R^{16}$ and $R^{17}$, which may be the same or different, each represents a hydrogen atom, an aliphatic group, an aromatic group, a heterocyclic group, or a $-(\text{Time})_t\text{DIG}$ group.

7. The color diffusion transfer photographic material as claimed in claim 2, wherein A represents

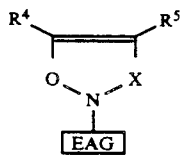

linked to $-(\text{Time})_t\text{DIG}$ through at least one of $R^4$, $R^5$ and EAG; EAG has the same definition as in claim 2; X represents a divalent linking group; and $R^4$ and $R^5$, which may be the same or different, each represents a hydrogen atom or a substituent, provided that two substituent groups $R^4$ and $R^5$ may be linked to form a saturated or unsaturated carbon ring or heterocyclic ring.

8. The color diffusion transfer photographic material as claimed in claim 7, wherein said divalent linking group represented by X is a

or $-SO_2-$ group; $R^4$ represents a hydrogen atom, a substituted or unsubstituted alkyl group, a substituted or unsubstituted aryl group, or a substituted or unsubstituted heterocyclic ring group; and $R^5$ represents a hydrogen atom, a substituted or unsubstituted alkyl group, a substituted or unsubstituted aryl group, or a substituted or unsubstituted heterocyclic ring group.

9. The color diffusion transfer photographic material as claimed in claim 8, wherein $R^4$ represents a group

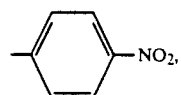

and $R^5$ represents a group

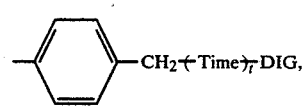

or a group

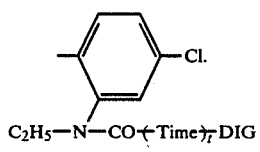

10. The color diffusion transfer photographic material as claimed in claim 1, wherein Time is represented by the following general formulae (T—1) to (T—4) and (T—10):

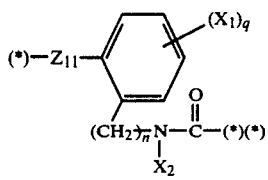 (T-1)

wherein $Z_{11}$ represents (*)—O—,

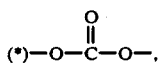

(*)—O—CH$_2$—O—, (*)—O—CH$_2$—, (*)—O—CH$_2$—S—,

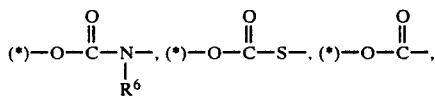

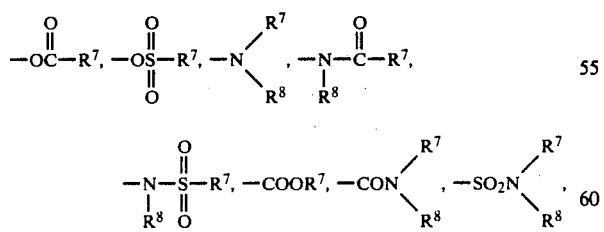

a cyano group, a halogen atom, or a nitro group, wherein $R^7$ and $R^8$, which may be the same or different, each has the same definition as $R^6$;

$X_2$ has the same definition as $R^6$;

q is an integer of 1 to 4, provided that when q is at least 2, the plural substituents represented by $X_1$ may be the same or different, and plural $X_1$ groups may be linked to form a ring; and n is 0, 1 or 2;

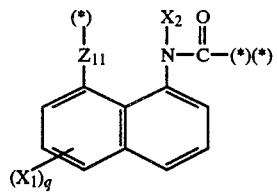 (T-2)

wherein $Z_{11}$, $X_1$, $X_2$ and q each has the same definition as in general formula (T—1);

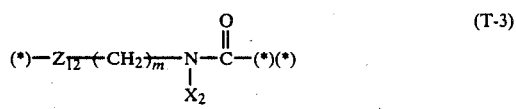 (T-3)

wherein $Z_{12}$ represents (*)—O—,

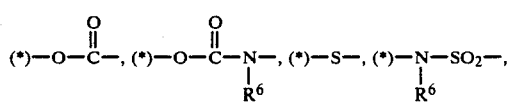

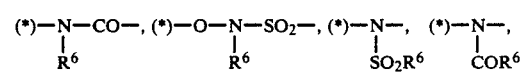

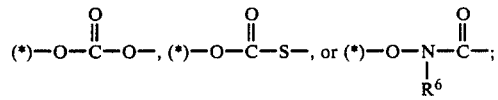

m is an integer of 1 to 4; and $R^6$ and $X_2$ each has the same definition general formula (T—1);

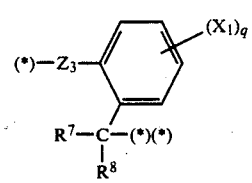 (T-4)

wherein $Z^3$ represents (*)—O—,

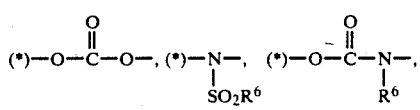

(*)—O—CH$_2$—O—, or (*)—O—CH$_2$—S—; and $R^6$, $R^7$, $R^8$, $X_1$ and q each has the same definition as in general formula (T—1);

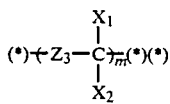 (T-10)

wherein $X_1$ and $X_2$ each has the same definition as in general formula (T—1); $Z^3$ has the same definition as in general formula (T—4); and m is an integer of 1 to 4;

wherein (*) represents the position by which Time is linked to A of general formula (I) and (*) (*) represents the position by which Time is linked to DIG of general formula (I).

11. The color diffusion transfer photographic material as claimed in claim 10, wherein said heterocyclic ring in each of general formulae (T—1) to (T—4) is

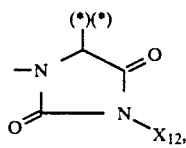

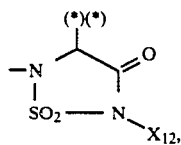

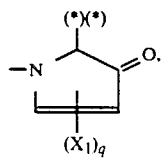

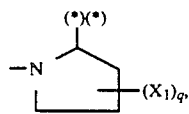

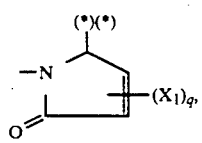

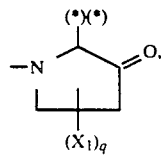

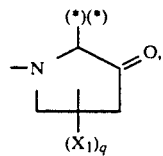

and

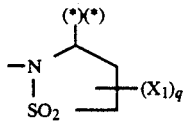

wherein $X_1$ and q each has the same definition as in general formula (T—1); and $X_{12}$ represents a hydrogen atom, an aliphatic group, an aromatic group, an acyl group, a sulfonyl group, an alkoxycarbonyl group, a sulfamoyl group, a heterocyclic ring group or a carbamoyl group.

12. The color diffusion transfer photographic material as claimed in claim 10, wherein said aliphatic group represented by $X_1$, $X^2$, $R^6$, $R^7$, and $R^8$ contains from 1 to 20 carbon atoms, said aromatic group represented by $X_1$, $X^2$, $R^6$, $R^7$, and $R^8$ contains 6 to 20 carbon atoms, and said heterocyclic ring group represented by $X_1$, $X^2$, $R^6$, $R^7$, and $R^8$ is a 5-membered or 6-membered heterocyclic ring containing at least one hetero atom selected from a nitrogen atom, an oxygen atom and a sulfur atom.

13. The color diffusion transfer photographic material as claimed in claim 12, wherein said aromatic group is a substituted or unsubstituted phenyl group and said heterocyclic ring group is selected from the group consisting of a pyridyl group, a furyl group, a thienyl group, a triazolyl group, an imidazolyl group, a pyrazolyl group, a thiazolyl group, an oxadiazolyl group and a pyrrolidinyl group.

14. The color diffusion transfer photographic material as claimed in claim 1, wherein said dye-releasing redox compound is represented by the following general formula (R—I):

$$Y-(L)_s-X \qquad (R-I)$$

wherein Y represents a redox nucleus; X represents a dye-forming group; L represents a divalent linking group selected from the group consisting of an alkylene group having 1 to 6 carbon atoms, an alkylidene group having 1 to 6 carbon atoms, an arylene group, a heterocyclic ring group, —O—, —S—, —SO$_2$—, and —NR$^{10}$, wherein R$^{10}$ represents a hydrogen atom, an alkyl group, —CO—, —CONH—, or —SO$_2$NH—; and s is 0 or 1.

15. The color diffusion transfer photographic material as claimed in claim 14, wherein said dye-releasing redox compound is represented by the following general formulae (Y—I) or (Y—II):

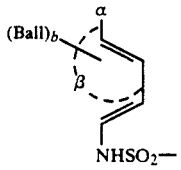 (Y-I)

wherein β represents a nonmetallic atomic group necessary for forming a substituted or unsubstituted benzene ring, a benzene ring condensed with a carbon ring or a benzene ring condensed with a heterocyclic ring; α represents a group OG$^1$ or —NHG$^2$, wherein G$^1$ represents a hydrogen atom or a group capable of being hydrolyzed to a hydroxyl group; G$^2$ represents a hydrogen atom, an alkyl group having 1 to 22 carbon atoms, Ball represents a ballasting group; and b is an integer of 0, 1 or 2, provided that the compound represented by general formula (Y—I) contains at least one group capable of rendering said compound nondiffusible;

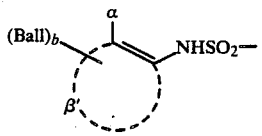

(Y-II)

wherein $\beta'$ represents an atomic group necessary for forming a substituted or unsubstituted carbon ring, a carbon ring condensed with a second carbon ring, or a carbon ring condensed with a heterocyclic ring; and Ball, $\alpha$ and b each has the same definition as in general formula (Y—I).

* * * * *